Figure 1:
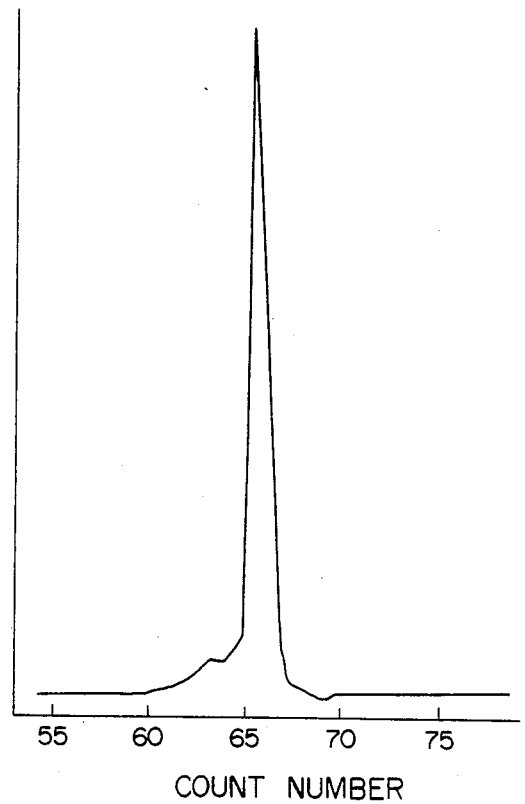

United States Patent [19]

Mizui et al.

[11] Patent Number: 4,570,024

[45] Date of Patent: Feb. 11, 1986

[54] NOVEL SUBSTITUTED AROMATIC HYDROCARBONS, PROCESSES FOR PRODUCTION THEREOF, AND USE THEREOF

[75] Inventors: Kinya Mizui; Masami Takeda; Yoshimi Ozaki, all of Ohtake; Ryosuke Tomita, Iwakuni, all of Japan

[73] Assignee: Mitsui Petrochemical Industries, Ltd., Tokyo, Japan

[21] Appl. No.: 731,388

[22] Filed: May 7, 1985

[30] Foreign Application Priority Data

| May 7, 1984 | [JP] | Japan | 59-89526 |
| Nov. 16, 1984 | [JP] | Japan | 59-240565 |
| Dec. 7, 1984 | [JP] | Japan | 59-257440 |
| Mar. 4, 1985 | [JP] | Japan | 60-41289 |

[51] Int. Cl.$^4$ .................................................. C07C 13/38
[52] U.S. Cl. ............................................ 585/24; 585/25; 585/21; 585/22; 585/23; 568/716
[58] Field of Search ................. 585/24, 25, 21, 22, 585/23, 446, 266, 26, 27; 568/716

[56] References Cited

U.S. PATENT DOCUMENTS

| 3,419,631 | 12/1968 | Van Venrooy | 585/25 |
| 3,660,508 | 5/1972 | Dart et al. | 585/23 |
| 3,760,020 | 9/1973 | Moore | 585/25 |
| 3,916,017 | 10/1975 | Shepherd, Jr. | 585/23 |

FOREIGN PATENT DOCUMENTS 691904-3 12/1968 Netherlands .................. 585/23

Primary Examiner—John Doll
Assistant Examiner—A. Pal
Attorney, Agent, or Firm—Sherman and Shalloway

[57] ABSTRACT

An aromatic hydrocarbon in which at least one hydrogen atom on the ring is substituted by a group selected from the class consisting of unsubstituted or lower alkyl-substituted tricyclo[5.2.1.0$^{2,6}$]dec-3-yl, tricyclo[5.2.1.0$^{2,6}$]dec-4-yl, tetracyclo[6.2.1.1$^{3,6}$.0$^{2,7}$]dodec-4-yl and tetracyclo[6.2.1.1$^{3,6}$.0$^{2,7}$]dodec-5-yl groups, or its hydrogenation product.

The compound is prepared by reacting an aromatic hydrocarbon having at least one hydrogen atom on the ring with a compound selected from the group consisting of unsubstituted or lower alkyl-substituted tricyclo[5.2.1.0$^{2,6}$]dec-3-ene and tetracyclo[6.2.1.1$^{3,6}$.0$^{2,7}$]dodec-4-ene in the presence of a Friedel-Crafts catalyst, or hydrogenating the thus-obtained compound in the presence of a hydrogenation catalyst.

The compound is useful as an additive for adhesives.

11 Claims, 12 Drawing Figures

COUNT NUMBER

COUNT NUMBER

COUNT NUMBER

COUNT NUMBER

NOVEL SUBSTITUTED AROMATIC HYDROCARBONS, PROCESSES FOR PRODUCTION THEREOF, AND USE THEREOF

This invention relates to substituted aromatic hydrocarbons and their hydrogenation products, processes for production thereof and use thereof in applications utilizing their adhesive properties.

More specifically, this invention relates to tricyclodecyl- or tetracyclododecyl-substituted aromatic hydrocarbons and their hydrogenation products, processes for production thereof, and use thereof in applications utilizing their adhesive properties.

It is known that a polymer represented by the following formula

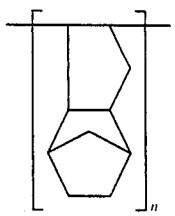

can be produced by selectively hydrogenating dicyclopentadiene (tricyclodecadiene) represented by the following formula (hydrogenating only the double bond of the norbornene ring)

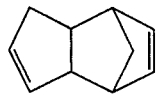

to form dihydroxycyclopentadiene represented by the following formula

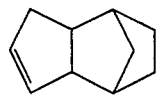

and thereafter polymerizing it, and the resulting polymer has the properties of a tackifier (see Japanese Patent Publication No. 11818/1972).

However, tricyclododecyl- or tetracyclododecyl-substituted aromatic hydrocarbons have not been known heretofore.

It is an object of this invention therefore to provide novel and useful tricyclodecyl- or tetracyclododecyl-substituted aromatic hydrocarbons and their hydrogenation products.

Another object of this invention is to provide the use of the aforesaid novel substituted aromatic hydrocarbons or their hydrogenation products as adhesive additives such as a softening agent or a tackifier by utilizing their adhesive properties.

Still another object of this invention is to provide industrially advantageous processes for producing the aforesaid novel and useful substituted aromatic hydrocarbons and their hydrogenation products.

Other objects and advantages of this invention will become apparent from the following description.

According to this invention, the above objects and advantages are achieved by an aromatic hydrocarbon in which at least one hydrogen atom on the ring is substituted by a group selected from the class consisting of unsubstituted or lower alkyl-substituted tricyclo[5.2.1.0$^{2,6}$]dec-3-yl, tricyclo[5.2.1.0$^{2,6}$]dec-4-yl, tetracyclo[6.2.1.1$^{3,6}$.0$^{2,7}$]dodec-4-yl and tetracyclo[6.2.1.1$^{3,6}$.0$^{2,7}$]dodec-5-yl groups, or its hydrogenation product.

According to this invention, the novel substituted aromatic hydrocarbons of this invention are produced by reacting an aromatic hydrocarbon having at least one hydrogen atom on the ring with a compound selected from the group consisting of unsubstituted or lower alkyl-substituted tricyclo[5.2.1.0$^{2,6}$]dec-3-enes and tetracyclo[6.2.1.1$^{3,6}$.0$^{2,7}$]dodec-4-enes in the presence of a Friedel-Crafts catalyst to substitute at least one hydrogen atom on the ring by an unsubstituted or lower alkyl-substituted tricyclodecyl or tetracyclododecyl group derived from said compounds.

The hydrogenation products of the substituted aromatic hydrocarbons can be produced by catalytically hydrogenating the substituted aromatic hydrocarbons so obtained.

The aromatic hydrocarbon used as one starting material in the process of this invention should have at least one hydrogen atom on the ring. The aromatic hydrocarbon may have 6 to 18 carbon atoms, preferably 6 to 15 carbon atoms, more preferably 6 to 10 carbon atoms. Examples of the aromatic hydrocarbon in which the ring hydrogen atom is unsubstituted are benzene, naphthalene, anthracene, biphenyl, terphenyl and indane. Aromatic hydrocarbons in which the ring hydrogen atom is substituted by, for example, a lower alkyl group having 1 to 6 carbon atoms or a hydroxyl group may also be used as the starting material. Examples of such ring-substituted aromatic hydrocarbons include toluene, o-xylene, m-xylene, p-xylene, ethylbenzene, n-propylbenzene, isopropylbenzene, o-ethyltoluene, m-ethyltoluene, p-ethyltoluene, n-butylbenzene, isobutylbenzene, sec-butylbenzene, t-butylbenzene, diethylbenzene, 1-methylnaphthalene, 2-methylnaphthalene, 9-methylanthracene, phenol, o-cresol, m-cresol, p-cresol, 2,6-dimethylphenol, 2,3-dimethylphenol, 2,4-dimethylphenol, 2,5-dimethylphenol, 3,4-dimethylphenol, 3,5-dimethylphenol, 3-methyl-6-isopropylphenol, 2,6-di-tert-butylphenol, p-phenylphenol, bisphenol A, bisphenol AP, bisphenol F, alpha-naphthol and beta-naphthol.

Preferred starting aromatic hydrocarbons are benzene, toluene, ethylbenzene, o-, m- or p-xylene, phenol, o-, m- or p-cresol, 2,6-tert-butylphenol, bisphenol A, alpha-naphthol and beta-naphthol.

The other starting compound is selected from substituted or lower alkyl-substituted tricyclo[5.2.1.0$^{2,6}$]dec-3-ene and tetracyclo[6.2.1.1$^{3,6}$.0$^{2,7}$]dodec-4-ene.

The unsubstituted or lower alkyl-substituted tricyclo[5.2.1.0$^{2,6}$]dec-3-ene may preferably be a compound (particularly unsubstituted) represented by the following formula (1)'

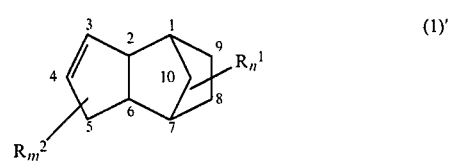

wherein $R^1$ is a lower alkyl group substituted at at least one of 1- and 7- to 10-positions, $R^2$ is a lower alkyl group substituted at at least one of 2- to 6-positions, n is 0 or an integer of 1 to 5 and m is 0 or an integer of 1 to 5, provided that when n is an integer of 2 to 5, the $R^1$ groups may be identical or different and when m is an integer of 2 to 5, the $R^2$ groups may be identical or different.

The lower alkyl groups for $R^1$ and $R^2$ usually have 1 to 6 carbon atoms and may be linear or branched. Examples include methyl, ethyl, n-propyl, iso-propyl, n-butyl, iso-butyl, sec-butyl, t-butyl, n-pentyl and n-hexyl. Of the compounds of formula (1)', preferred lower alkyl-substituted compounds include, for example, monolower alkyl-substituted compounds in which the alkyl group is substituted at the 3-, 4-, 5-, 7-, 8-, 9-, or 10-position, and di-lower alkyl-substituted compounds in which the alkyl groups are substituted at the 5,7-, 5,8-, 5,9-, 5,10-, 4,7-, 4,8-, 4,9-, 3,8-, 3,9- or 1,4-positions.

The tricyclo[5.2.1.0$^{2,6}$]dec-3-enes can be produced by a method known per se which comprises dimerizing cyclopentadienes to dicyclopentadienes and selectively hydrogenating the dicyclopentadienes. Naturally, it is preferred to use such tricyclo[5.2.1.0$^{2,6}$]dec-3-enes in a highly purified form in the process of this invention. But they may also be used while containing subsidiary components mixed during the production, for example a polymerizable component such as cyclopentene, tricyclo[5.2.1.0$^{2,6}$]dec-8-ene, and partially hydrogenated products of di- or higher oligomers of cyclopentadiene, or a nonpolymerizable component such as tricyclo[5.2.1.0$^{2,6}$]decanes. If the tricyclo[5.2.1.0$^{2,6}$]dec-3-enes have a purity of at least about 60% by weight, the reaction in the process of this invention proceeds without any problem.

The unsubstituted or lower alkyl-substituted tetracyclo[6.2.1.1$^{3,6}$.0$^{2,7}$]dodec-4-ene may preferably be a compound (particularly unsubstituted) represented by the following formula (3)'

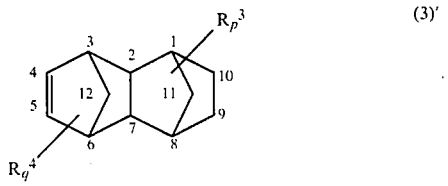

wherein $R^3$ is a lower alkyl group substituted at at least one of 1-, 2- and 7- to 11-positions, $R^4$ is a lower alkyl group substituted at at least one of 3- to 6- and 12-positions, p is 0 or an integer of 1 to 7 and q is 0 or an integer of 1 to 5, provided that when p is an integer of 2 to 7, the $R^3$ groups may be identical or different and when q is an integer of 2 to 5, the $R^4$ groups may be identical or different.

Examples of the lower alkyl groups for $R^3$ and $R^4$ in formula (3)' may be the same as those given hereinabove for $R^1$ and $R^2$ in formula (1)'. Of the compounds of formula (3)', preferred lower alkyl-substituted compounds are mono-lower alkyl-substituted compounds in which the alkyl group is substituted at the 1-, 3-, 6-, 8-, or 9-position, and di-lower alkyl-substituted compounds which the alkyl groups are substituted at the 1,6-, 3,8-, 9,10- or 11,12-positions.

The tetracyclo[6.2.1.1$^{3,6}$.0$^{2,7}$]dodec-4-enes can be easily produced by a known method which comprises condensing norbornenes with cyclopentadienes. Needless to say, it is preferred to use the tetracyclo[6.2.1.1$^{3,6}$.0$^{2,7}$]-dodec-4-enes in a highly purified form. But they may be used while containing a non-polymerizable component or a polymerizable component such as norbornenes (e.g., 2-methyl-norbornene), cycloalkenes (e.g., methylcyclopentene and methylcyclohexene), and tricyclo[5.2.1.0$^{2,6}$]dec-3-enes (e.g., 0-methyl-tricyclo[5.2.1.0$^{2,6}$]dec-3-enes. Preferably, the above compounds have a purity of at least about 60% by weight, preferably at least 65% by weight, especially preferably 70% by weight. The presence of the polymerizable component may react with the aromatic hydrocarbon as does the tetracyclo[6.2.1.1$^{3,6}$.0$^{2,7}$]-4-dodecene. Hence, the substituted aromatic hydrocarbon cannot be obtained in pure form, and has sufficient adhesive property in the form of a mixture.

The reaction in the process of this invention is carried out by using 1 mole of the starting aromatic hydrocarbon and usually about 0.5 to 50 moles, preferably about 1.2 to 10 moles, of the tricyclo[5.2.1.0$^{2,6}$]dec-3-ene and/or tetracyclo[6.2.1.1$^{3,6}$.0$^{2,7}$]dodec-4-ene, and treating these starting compounds in the presence of a Friedel-Crafts catalyst, optionally in an inert solvent.

Examples of the Friedel-Crafts catalyst that can be used in this invention include Lewis acids such as $AlCl_3$, $AlBr_3$, $BF_3$, $SnCl_4$, $SnBr_4$, $FeCl_3$, $BeCl_2$, $CdCl_2$, $ZnCl_2$, $BCl_3$, $BBr_3$, $TiCl_4$, $TiBr_4$, $ZrCl_4$, and alkyl aluminum dichlorides, dialkyl aluminum monochloride, alkyl aluminum sesquichloride, and complexes of Lewis acids such as a complex of $BF_3$ with an alcohol, phenol or ether or a three-component complex of $AlCl_3$, an aromatic hydrocarbon and a hydrogen halide. Of these, $BF_3$, $AlCl_3$, and their complexes are preferred. The amount of the catalyst used differs depending upon its type, the types or purifies of the starting materials, the reaction temperature, etc. Generally, it is used in a proportion of about 1 to about 50 mole % based on the starting aromatic hydrocarbon.

Usually, the reaction is carried out in the absence of a solvent. If desired, an inert solvent may be used. The inert solvent may preferably be aliphatic hydrocarbons such as pentane, hexane, heptane, decane and dodecane, halogenated aliphatic hydrocarbons such as dichloromethane, ethyl chloride, and 1,2-dichloroethane, and aromatic hydrocarbons which do not participate in the alkylation reaction such as chlorobenzene and nitrobenzene.

The reaction is carried out under atmospheric or elevated pressure at a temperature of generally about −10° to 200° C., preferably about 0° to 150° C. for about 0.5 to 10 hours, preferably 1 to 10 hours. The procedure employed is to maintain the starting materials and as required the inert solvent at a predetermined temperature and pressure, and then to add the catalyst while the mixture is stirred. After performing the reaction for a predetermined period of time, the remaining catalyst is removed in a customary manner and the unreacted compounds and the reaction solvent are removed by distillation. As a result, the desired substituted aromatic hydrocarbon can be obtained. Since the starting tricyclo[5.2.1.0$^{2,6}$]dec-3-ene or tetracyclo[6.2.1.1$^{3,6}$.0$^{2,7}$]dodec-4-ene alone hardly polymerizes, the use of this starting material in high purity can give the desired substituted aromatic hydrocarbon of relatively high purity.

Thus, the process of this invention can give the desired substituted aromatic hydrocarbon of this invention in which at least one hydrogen atom on the ring is substituted by a group selected from the class consisting of unsubstituted or lower alkyl-substituted tricyclo[5.2.1.0$^{2,6}$]dec-3-yl, tricyclo[5.2.1.0$^{2,6}$]dec-4-yl, tetracyclo[6.2.1.1$^{3,6}$.0$^{2,7}$]dodec-4-yl and tetracyclo[6.2.1.1$^{3,6}$.0$^{2,7}$]dodec-5-yl groups.

The hydrogenation product of the substituted aromatic hydrocarbon can be produced by hydrogenating the substituted aromatic hydrocarbon in the presence of a hydrogenation catalyst.

The hydrogenation is carried out in a suitable solvent in the presence of a suitable hydrogenation catalyst. The hydrogenation catalyst may be metals of Group VI or VII of the periodic table or compounds of these metals. Specific examples include nickel, chromium, palladium, platinum, cobalt, osmium, rhenium, ruthenium, Raney nickel, nickel sulfide, nickel oxide, copper chromite, cobalt molybdenum, molybdenum sulfide, platinum oxide, cobalt oxide, rhenium oxide, ruthenium oxide, sponge iron and iron oxide. Examples of the solvent are aliphatic and alicyclic hydrocarbons having 5 to 20 carbon atoms, especially 5 to 10 carbon atoms, such as pentane, hexane, heptane, isoheptane, octane, isooctane, cyclohexane, methylcyclohexane and decalin.

If the substituted aromatic hydrocarbon to be hydrogenated is a liquid having a low viscosity at the reaction temperature, it can be hydrogenated without using a solvent.

The hydrogenation is carried out by a batch or continous method by treating the substituted aromatic hydrocarbon with hydrogen gas at a temperature of usually 20° to 300° C., preferably about 100° to 240° C. under reduced or elevated pressure, generally atmospheric presure to about 300 kg/cm$^2$-G, preferably about 10 to 150 kg/cm$^2$-G for a period of about 10 minutes to about 24 hours, preferably about 10 minutes to about 7 hours.

After the hydrogenation, the reaction mixture can be separated in a customary manner, for example by distillation, into the solvent, the unreacted substituted aromatic hydrocarbon and the hydrogenated substituted aromatic hydrocarbon. But when the hydrogenated substituted aromatic hydrocarbon is to be used as an additive for adhesives, the unreacted substituted aromatic hydrocarbon needs not always to be separated, but the hydrogenated substituted aromatic hydrocarbon containing the unreacted substituted aromatic hydrocarbon may be used as such adhesive additive. Preferably, the total ratio of hydrogenation of the mixture is adjusted to at least 10%, especially at least 40%.

By the process described above, the present invention provides an aromatic hydrocarbon in which at least one hydrogen atom on the ring is substituted by a group selected from the class consisting of unsubstituted or lower alkyl-substituted tricyclo[5.2.1.0$^{2,6}$]dec-3-yl, tricyclo[5.2.1.0$^{2,6}$]dec-4-yl, tetracyclo[6.2.1.1$^{3,6}$.0$^{2,7}$]dodec-4-yl and tetracyclo[6.2.1.1$^{3,6}$.0$^{2,7}$]dodec-5-yl groups, or its hydrogenation product.

The aforesaid unsubstituted or lower alkyl-substituted tricyclo[5.2.1.0$^{2,6}$]dec-3-yl group is represented, or example, by the following formula (1)

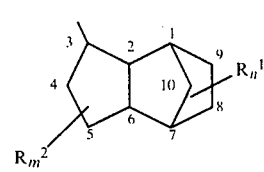
(1)

wherein $R^1$ is a lower alkyl group substituted at at least one of 1- and 7- to 10-positions, $R^2$ is a lower alkyl group substituted at at least one of 2- to 6-positions, n is 0 or an integer of 1 to 5 and m is 0 or an integer of 1 to 5, provided that when n is an integer of 2 to 5, the $R^1$ groups may be identical or different and when m is an integer of 2 to 5, the $R^2$ groups may be identical or different.

The unsubstituted or lower alkyl-substituted tricyclo[5.2.1.0$^{2,6}$]dec-4-yl group is represented, for example, by the following formula (2)

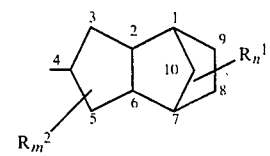
(2)

wherein $R^1$, $R^2$, n and m are as defined in formula (1).

The tricyclo[5.2.1.0$^{2,6}$]dec-3-yl group and the tricyclo[5.2.1.0$^{2,6}$]dec-4-yl group are derived from the tricyclo[5.2.1.0$^{2,6}$]dec-3-enes of formula (1)'.

The unsubstituted or lower alkyl-substituted tetracyclo[6.2.1.1$^{3,6}$.0$^{2,7}$]dodec-4-yl group is represented, for example, by the following formula (3)

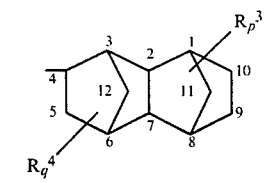
(3)

wherein $R^3$ is a lower alkyl group substituted at at least one of 1-, 2- and 7- to 11-positions, $R^4$ is a lower alkyl group substituted at at least one of 3- to 6- and 12-positions, p is 0 or an integer of 1 to 7 and q is 0 or an integer of 1 to 5, provided that when p is an integer of 2 to 7, the $R^3$ groups may be identical or different and when q is an integer of 2 to 5, the $R^4$ groups may be identical or different.

The unsubstituted or lower alkyl-substituted tetracyclo[6.2.1.1$^{3,6}$.0$^{2,7}$]dodec-5-yl is represented by the following formula (4)

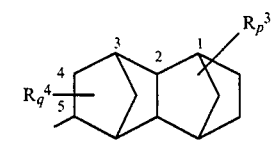
(4)

wherein $R^3$, $R^4$, p and q are as defined in formula (3).

The tetracyclo[6.2.1.1$^{3,6}$.0$^{2,7}$]dodec-4-yl group and tetracyclo[6.2.1.1$^{3,6}$.0$^{2,7}$]dodec-5-yl group are derived from the tetracyclo[6.2.1.1$^{3,6}$.0$^{2,7}$]dodec-4-enes of formula (3)'.

A group of preferred compounds in accordance with this invention are, for example, aromatic hydrocarbons represented by the following formula (A)

 (A)

wherein Ar represents an aromatic hydrocarbon ring, R is a lower alkyl group having 1 to 6 carbon atoms or a hydroxyl group, X is a group selected from the class consisting of unsubstituted or $C_1$–$C_6$ alkyl-substituted tricyclo[5.2.1.0$^{2,6}$]dec-3-yl, tricyclo [5.2.1.0$^{2,6}$]dec-4-yl, tetracyclo[6.2.1.1$^{3,6}$.0$^{2,7}$]dodec-4-yl and tetracyclo[6.2.1.1$^{3,6}$.0$^{2,7}$]dodec-5-yl groups, r is 0, 1, 2 or 3, and l is 1, 2 or 3; or hydrogenation products thereof.

In formula (A), The aromatic hydrocarbon ring Ar may, for example, be a benzene, naphthalene, anthracene, biphenyl, terphenyl or indane ring. Benzene and naphthalene rings are preferred and the benzene ring is specially preferred.

Examples of the compounds of this invention represented by formula (A) are mono-X benzene, 1,3-di-X benzene, 1,3,5-tri-X benzene, o-X toluene, p-X toluene, 2,4-di-X toluene, 3,5-di-X toluene, 2,4,6-tri-X toluene, 5-X m-xylene, 4-X m-xylene, 4,6-di-X m-xylene, 2,4-di-X m-xylene, 4-X o-xylene, 2-X p-xylene, o-X ethylbenzene, p-X ethylbenzene, 2,4-di-X ethylbenzene, 2,4-6-tri-X ethylbenzene, p-X cumene, 4-methyl-3-X ethylbenzene, 2-methyl-5-X ethylbenzene, o-X cumene, 2,4,6-tri-X cumene, 1-X naphthalene, 1-X anthracene, 1-methyl-4-X naphthalene, 1-methyl-2-X naphthalene, 1-methyl-3-X naphthalane, 1-methyl-5-X naphthelene, 2,4,6-tri-X phenol, 2-methyl-4,6-di-X phenol, 2,6-dimethyl-4-X phenol, 2-ethyl-4,6-di-X phenol, 2,6-diethyl-4-X phenol, 2-isopropyl-4,6-di-X phenol, 2,6-diisopropyl-4-X phenol, 2,4-di-X alpha-naphthol, 1,4-di-X beta-naphthol, 2,2-bis[4-hydroxy-3,5-di-X phenyl]-propane, 2,4,6-tri(8-methyl-tri-X)phenol, and 2,6-diisopropyl-4-(8-methyl-tri-X)phenol.

Examples of the hydrogenation products of these compounds include mono-X cyclohexane, 1,3-di-X cyclohexane, 1,3,5-tri-X cyclohexane, 1-methyl-3-X cyclohexane, 1-methyl-2-X cyclohexane, 1-methyl-4-X cyclohexane, 1-methyl-2,4-di-X cyclohexane, 1-methyl-3,5-di-X cyclohexane, 1-methyl-2,4,6-tri-X cyclohexane, 1,3-dimethyl-5-X cyclohexane, 1,3-dimethyl-4-X cyclohexane, 1,3-dimethyl-4,6-di-X cyclohexane, 1,3-dimethyl-2,4-di-X cyclohexane, 1,2-di-methyl-4-X cyclohexane, 1,4-dimethyl-2-X cyclohexane, 1-ethyl-3-X cyclohexane, 1-ethyl-2-X cyclohexane, 1-ethyl-4-X cyclohexane, 1-ethyl-2,4-di-X cyclohexane, 1-ethyl-2,4,6-tri-X cyclohexane, 1-isopropyl-4-X cyclohexane, 1-methyl-2-X-4-ethyl cyclohexane, 1-methyl-2-ethyl-4-X cyclohexane, 1-ethyl-4-X cyclohexane, 1-isopropyl-2-X cyclohexane, 1-isopropyl- 2,4,6-tri-X cyclohexane, 1-X-1,2,3,4-tgetrahydronaphthalene, 2-X-5,6,7,8-tetrahydronaphthalene, 2-X decahydronaphthalene, 1-X tetradecahydroanthracene, 1-methyl-4-X-5,6,7,8-tetrahydronaphthalene, 1-methyl-2-X-5,6,7,8-tetrahydronaphthalaen, 1-methyl-3-X-5,6,7,8-tetrahydronaphthalene, 1-methyl-5-X-5,6,7,8-tetrahydronaphthalene, 1-methyl-4-X-1,2,3,4-tetrahydronaphthalene, 1-methyl-2-X-1,2,3,4-tetrahydronaphthalene, 1-methyl-3-X-1,2,3,4-tetrahydronaphthalene, 1-methyl-5-X-1,2,3,4-tetrahydronaphthalene, 1-methyl-4-X decahydronaphthalene, 1-methyl-2-X decahydronaphthalene, 1-methyl-3-X decahydronaphthalene, 1-methyl-5-X decahydronaphthalene, 1-hydroxy-2,4,6-tri-X cyclohexane, 1-hydroxy-2-methyl-4,6-di-X cyclohexane, 1-hydroxy-2,6-dimethyl-4-X cyclohexane, 1-hydroxy-2-ethyl-4,6-di-X cyclohexane, 1-hydroxy-2,6-diethyl-4-X cyclohexane, 1-hydroxy-2-isopropyl-4,6-di-X cyclohexane, 1-hydroxy-2,6-diisopropyl-4-X cyclohexane, 1-hydroxy-2,4-di-X decahydronaphthalene, 2-hydroxy-1,4-di-X decahydronaphthalene, 2,2-bis[4-hydroxy-3,5-di-X cyclohexyl]-propane, 1-hydroxy-2,4,6-tri(8-methyl-tri-X)cyclohexane, and 1-hydroxy-2,6-diisopropyl-4-(8-methyl-tri-X) cyclohexane.

The novel substituted aromatic hydrocarbons (A) of this invention have excellent adhesive properties, and are useful as hot-melt adhesives, additives for pressure-sensitive adhesives, namely as a tackifier or a softening agent.

Adhesive compositions are generally classified as hot-melt adhesives comprising a substrate resin such as ethylene/vinyl acetate copolymer, a tackifier and as required, a wax and other additives, and pressure-sensitive adhesives comprising a substrate resin such as natural rubber or synthetic rubber, a tackifier and as required a solvent and other additives. The hot-melt adhesives are used as bonding agents or coating agents in the field of book binding, can making, wood working, lamination, sheet formation, coating, etc. The pressure-sensitive adhesives are generally coated on such substrates as paper, cloths or plastic films and used as adhesive tapes or labels. In either type, the tackifer is added to the substrate resin. The tackifier for the hot-melt adhesives are required to have good thermal stability, light stability and color hues in addition to having good compatibility with the substrate resins such as ethylene/vinyl acetate copolymer and waxes, high adhesiveness and flexibility and moderate melt viscosity. The tackifier for the pressure-sensitive adhesives is required to have in combination excellent compatibility with such substrate resins as natural or synthetic rubbers, good solubility in solvents, good chemical stability, excellent weatherability, good color hues and freedom from strong odors.

When the compounds (A) of this invention are used as a tackifier or softening agent for pressure-sensitive adhesives, rubbery polymers are preferably used as the substrate resins. Examples of the rubbery polymers include natural rubber, styrene/butadiene copolymer rubber, polybutadiene, polyisoprene, polyisobutylene, butyl rubber, polychloroprene, ethylene/propylene copolymer, ethylene/propylene/alpha-olefin copolymer rubbers, ethylene/propylene/diene copolymer, stryene/butadiene/styrene block copolymer, styrene/isoprene/styrene block copolymer, hydrogenated styrene/butadiene/styrene block copolymer (SEBS), and hydrogenated styrene/isoprene/styrene block copolymer. The styrene/butadiene/styrene block copolymer, styrene/isoprene/styrene block copolymer and hydrogenation products of these copolymers are especially preferred.

When the compounds (A) of this invention are used as a tackifier or softener for hot-melt adhesives, ethylene/vinyl acetate copolymer, polyethylene, polypropylene, ethylene/propylene copolymer, ethylene/acrylic acid copolymer, ethylene/acrylate copolymers, polyesters, polyamides and polyvinyl acetate may, for example, be used as the substrate resin. The ethylene/vinyl acetate copolymer and ethylene/acrylate copolymers are especially preferred.

When the compound (A) of this invention is used as a tackifier for a hot-melt adhesive composition, its amount is usually 20 to 300 parts by weight, preferably 30 to 200 parts by weight, per 100 parts by weight of the substrate resin. As a tackifier for a pressure-sensitive adhesive, it is used generally in an amount of 20 to 200 parts by weight, preferably 30 to 150 parts by weight, per 100 parts by weight of the substrate resin. As a softening agent, the compound (A) of this invention is used in an amount of usually 2 to 30 parts by weight for the hot-melt adhesive composition, and 10 to 100 parts by weight for the pressure-sensitive adhesive, both per 100 parts by weight of the substrate resin.

When the compound (A) of this invention is used as a tackifier for any of these adhesives, another softening agent may be used. When the compound (A) of this invention is used as a softening agent, another tackifier may be used. For example, dioctyl phthalate, dibutyl phthalate, machine oils, process oils, and polybutene may be used as the other softening agent, and rosin, rosin derivatives, terpene resins, alicyclic hydrocarbon resins, aliphatic hydrocarbon resins, aromatic hydrocarbon resins, and aliphatic-aromatic copolymer resins may, for example, be used as the other tackifier.

In addition to the compound (A) of this invention as a tackifier or softening agent and the substrate resin as essential ingredients, the adhesive composition containing the compound (A) of this invention may contain various additives as required. In the case of hot-melt adhesive compositions, examples of the additives are softening agents such as dioctyl phthalate and dibutyl phthalate, petroleum-type paraffin waxes having a melting point of about 40° to 65° C., waxes such as polyolefin waxes and microwaxes, antioxidants such as organic compounds of the phenol or bisphenol type and metal soaps. In the case of pressure-sensitive adhesives, examples of the additives include softening agents such as dioctyl phthalate, dibutyl phthalate, machine oils, process oils and polybutene, fillers such as calcium carbonate, zinc oxide, titanium oxide and silica, and antioxidants and stabilizers of the amine, ketone/amine or phenol type. These additives may be used in any desired amounts.

A hot-melt adhesive composition comprising the compound (A) of this invention is preferably prepared by a method which comprises stirring a mixture composed of the compound (A) as a tackifier, the substrate resin, and optionally the aforesaid additives under heat to prepare a uniform melt, and molding it under cooling into a shape suitable for a particular use, for example granules, flakes, pellets or rods.

The hot-melt adhesive composition is melted and coated. For example, in the bonding of corners of a molded article, the composition in the form of a rod is filled in a welding gun, melted and applied.

A pressure-sensitive adhesive may be prepared by a method which comprises kneading a mixture composed of the compound (A) of the invention as a tackifier, the substrate resin and as required, the various additives on a roll or dissolving it in a suitable solvent.

Since the compound (A) of the invention has excellent compatibility with the substrate resin, thermal stability, and color hues and the freedom from offensive odors, it gives a uniform hot-melt adhesive composition having excellent thermal stability and color hues and has the advantage that little odors are given off during the preparation of the hot-melt adhesive composition and during use. Since the compound (A) also has excellent weatherability in addition to the above desirable properties, it gives a uniform pressure-sensitive adhesive composition having excellent color hues and weatherability and reduced odors.

The adhesive compositions comprising the novel substituted aromatic hydrocarbons (A) of this invention will be specifically described in examples given hereinbelow.

The following examples illustrate the present invention more specifically. In these examples, the compounds (A) were evaluated by the following methods.
(1) Softening point: JIS K-5665
(2) Color hue: ASTM D 1544-58T; expressed by Gardner numbers.
(3) Molecular weight: Measured by a field desorption ionization mass spectrum analysis
(4) Refractive index: Measured by an Abbe refractometer at 25° C.
(5) Viscosity: Measured by Bismetron (made by Shibaura System Co., Ltd.) at 25°.

REFERENTIAL EXAMPLE 1

A $C_5$ fraction obtained by cracking of naphtha was heated at 150° C. for 3 hours to convert cyclopentadiene in it to dicyclopentadiene to obtain crude dicyclopentadiene composed of 20.1% of pentane and pentenes, 0.5% of benzene, 72.1% of dicyclopentadiene, 4.8% of isoprene-cyclopentadiene codimer and 2.5% of cyclopentadiene oligomer.

A metal autoclave was charged with 100 parts by weight (1710 g) of the crude dicyclopentadiene and 4 parts by weight of a tablet-shaped palladium hydrogenation catalyst (a product of Toyo C. C. I.; C31-1A), and the dicyclopentadiene was hydrogenated with stirring at 50° C. under a hydrogen pressure of 10 kg/cm$^2$ for 12 hours. The reaction mixture was filtered to remove the catalyst. The residue was distilled to obtain 90 parts by weight of a fraction containing tricyclo[5.2.1.0$^{2,6}$]dec-3-ene (9,10-dihydrodicyclopentadiene). Gas chromatographic analysis showed it to comprise 19.9% of pentanes, 70.9% of tricyclo[5.2.1.0$^{2,6}$]dec-3-ene, less than 0.1% of dicyclopentadiene, 4.5% of the hydrogenation product of isoprene-cyclopentadiene codimer, 2.1% of tricyclo[5.2.1.0$^{2,6}$]decane and 2.6% of unknown components.

EXAMPLE 1

A 500 ml four-necked flask equipped with a thermometer, a stirrer, a condenser and a dropping funnel was charged with 2 g of powdered anhydrous aluminum chloride in an atmosphere of nitrogen. With stirring, 94.5 g (0.5 mole) of the fraction containing tricyclo[5.2.1.0$^{2,6}$]dec-3-ene (purity 70.9%; obtained in Referential Example 1; the same fraction was used in the following Examples) was added through the dropping funnel, and the mixture was stirred at 70° C. for 2 hours. Methanol was added to stop the reaction. The reaction mixture was washed until it became neutral. It was then distilled to obtain 12.5 g of a nearly colorless distillate at a column top temperature of 150° to 155° C. and a pressure of 5 mmHg. The distillate had a molecular weight of 212 (theory 212) and showed the infrared spectrum given in FIG. 2. From these data, the product was determined to be tricyclo[5.2.1.0$^{2,6}$]dec-4-ylbenzene. The refractive index ($n_D^{25}$) was 1.5558.

Figure 2:
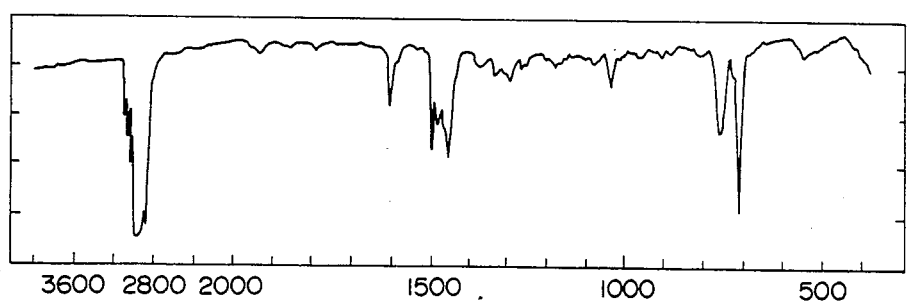

FIG. 1 is a liquid chromatogram of the reaction product obtained in Example 1 with count numbers plotted on the abscissa. FIG. 2 is an infrared absorption spectrum of the reaction product obtained in Example 1 with wave numbers plotted on the abscissa.

EXAMPLE 2

A 1-liter four-necked flask equipped with a thermometer, a stirrer, a condenser and a dropping funnel was charged with 400 g (4.35 moles) of toluene and 5 g of powdered anhydrous aluminum chloride. With stirring, 126.9 g (0.67 mole) of the fraction containing tricyclo[5.2.1.0$^{2,6}$]dec-3-ene (purity 70.9%) was added through the dropping funnel, and the mixture was heated at 70° C. for 5 hours. Methanol was added to stop the reaction. The reaction mixture was washed with water, and distilled to obtain 90 g of a colorless distillate at a boiling point of 158°–162° C./5 mmHg. The distillate had a molecular weight of 226 (theory 226). Its molecular weight and infrared spectrum showed it to be a mixture of 2-, 3- and 4-tricyclo[5.2.1.0$^{2,6}$]dec-4-yltoluenes. The refractive index ($n_D^{25}$) of 1.5582.

EXAMPLE 3

The same device as used in Example 2 was charged with 461 g (4.35 moles) of ethylbenzene and 5 g of powdered anhydrous aluminum chloride in an atmosphere of nitrogen. With stirring, 126.6 g (0.67 mole) of the fraction containing tricyclo[5.2.1.0$^{2,6}$]dec-3-ene (purity 70.9%) was added through the dropping funnel, and the mixture was heated at 60° C. for 2 hours. Methanol was added to terminate the reaction. The reaction mixture was washed until it became neutral. It was then distilled to obtain 115 g of a fraction having a boiling point of 170° to 174° C./5 mmHg. It had a molecular weight of 240 (theory 240). From its molecular weight and infrared spectrum, it was determined to consist mainly of a mixture of 2-, 3- and 4-tricyclo[5.2.1.0$^{2,6}$]dec-4-yl-ethylbenzenes.

EXAMPLE 4

The same device as used in Example 1 was charged with 79.5 g (0.75 mole) of mixed xylene (45% of m-xylene, 51% of ethylbenzene and 4% of o- and p-xylenes) and 3 g of powdered anhydrous aluminum chloride. With stirring, 283.5 g (1.5 moles) of the fraction containing tricyclo[5.2.1.0$^{2,6}$]dec-3-ene (purity 70.9%) was added through the dropping funnel, and the mixture was stirred at 60° C. for 2 hours. Methanol was added to terminate the reaction. The reaction mixture was washed until it became neutral. The unreacted material was then removed at a reactor temperature of 150° C. and a pressure of 20 mmHg. There was obtained a viscous liquid having a Gardner color number of 10, a viscosity at 25° C. of 10,800 cp and a refractive index ($n_D^{25}$) of 1.5482. Analysis showed it to consist of 59% by weight of a 1:1 adduct of tricyclo[5.2.1.0$^{2,6}$]dec-3-ene/mixed xylene adduct, 33% by weight of a 2:1 tricyclo[5.2.1.0$^{2,6}$]dec-3-ene/mixed xylene adduct, and 8% by weight of other components.

EXAMPLES 5–6

Example 4 was repeated under the conditions shown in Table 1. The amounts and properties of the reaction products obtained by removing the unreacted materials are shown in Table 1.

TABLE 1

| | Example | 4 | 5 | 6 |
|---|---|---|---|---|
| Reaction conditions | TCDE-containing fraction (g) | 283.5 | 283.5 | 283.5 |
| | Mixed xylene (g) | 79.5 | 63.6 | 45.4 |
| | AlCl$_3$ | 3.0 | 3.0 | 3.0 |
| | Temperature (°C.) | 60 | 90 | 90 |
| | Time (hours) | 2 | 2 | 2 |
| Amount of the product (g) | | 49 | 73 | 75 |
| Properties of the product | Softening point (°C.) | <5.0 | 11.0 | 22.5 |
| | Viscosity (cps/25° C.) | 10,800 | 40,300 | 57,800 |
| | Gardner color number | 10 | 11 | 12.5 |
| Composition of the product | Content of the 1:1 product (wt. %) | 59 | 37 | 33 |

EXAMPLE 7

A 1-liter four-necked flask equipped with a condenser, a stirrer, a thermometer and a gas introducing tube was charged with 400 g (4.35 moles) of toluene and 11 g (0.1 mole) of anhydrous aluminum chloride, and hydrogen chloride gas was blown into the flask with stirring. When the anhydrous aluminum chloride completely dissolved and became a uniform red solution (a three-component complex of alumuinum chloride, hydrogen chloride and toluene formed), the introduction of the hydrogen chloride gas was stopped. While maintaining the temperature at 20° C., 126.9 g (0.67 mole) of the fraction containing tricyclo[5.2.1.0$^{2,6}$]dec-3-ene (purity 70.9%) was added dropwise at 20° C. for 2 hours, further at 70° C. for 2 hours, and finally at 70° C. for 2 hours. The reaction mixture was poured into ice water, and the oil layer was washed with water until it became neutral. It was then distilled to obtain 121 g of a fraction having a boiling point of 158° to 162° C./5 mmHg. This product agreed in infrared absorption spectrum with the product obtained in Example 2.

EXAMPLE 8

The same device as used in Example 2 was charged with 400 g (4.35 moles) of toluene and 5 g of boron trifluoride diethyl etherate in an atmosphere of nitrogen. With stirring, 126.9 g (0.67 mole) of the fraction containing tricyclo[5.2.1.0$^{2,6}$]dec-3-ene (purity 70.9%) was added dropwise. The mixture was reacted at 20° C. for 2 hours and further at 70° C. for 3 hours. The catalyst was decomposed with a 10% aqueous solution of sodium hydroxide, and the reaction mixture was washed with water until it became neutral. It was then distilled to obtain 70 g of a fraction having a boiling point of 158° to 162° C./5 mmHg. This product agreed in infrared absorption spectrum with the product obtained in Example 2.

EXAMPLES 9–14

One hundred parts by weight of SIS block copolymer ("Kraiton TR-1107", a product of Shell Chemical Co.), 30 parts of a softening agent ("Shellflex 22R", a product of Shell Chemical Co., 3 parts by weight of a stabilizer ("Irganox 1010", a product of Ciba-Geigy), 70 parts by weight of a commercial aliphatic petroleum resin ("Hi-rez T-300X", a product of Mitsui Petrochemical Industries, Ltd.) and 30 parts by weight of each of the resins obtained in Examples 1 to 6 as a tackifier were kneaded by a kneader at 150° C. for 30 minutes to prepare an adhesive. The adhesive was heat-melted on a polyester film (thickness 25 microns) on a hot plate kept at 195° C., and coated to a thickness of 30±5 microns by using an applicator to prepare an adhesive tape.

The properties of the adhesive were evaluated by the following testing methods.

(1) Adhesion to corrugated cardboard

The adhesive tape was bonded at 5° C. to a corrugated cardboard (JIS K-7) by rolling a rubber roller having a weight of 850 g, and immediately then, peeled off. The surfacee condition of the corrugated cardboard was then examined, and evaluated on the following scale.

5: The entire surface of the cardboard was destroyed.
4: At least 30% of the surface of the cardboard was destroyed.
3: The destruction of the surface of the cardboard was clearly observed.
2: The destruction of the surface of the cardboard was slightly observed.
1: No surface destruction of the cardboard was observed.

(2) Tack (ball No.) Measured by the J. Dow method at 20° C.

(3) Adhesion strength (g/25 mm width) Measured by the method of JIS Z-1524 at 20° C.

(4) Cohesive force (mm/2HR) Measured by the method of JIS Z-1524 at 20° C.

(5) Corrugated cardboard holding power (hours)

A corrugated cardboard was used as an adherent. An adhesive tape (25×15 mm) prepared by using the compound of this invention was applied to the surface of the corrugated cardboard placed perpendicularly. A weight of 1 kg was suspended from the lower end of the tape applied to the cardboard, and the time (in hours) which elapsed until the weight and the applied tape dropped off from the cardboard was measured. During this test after suspending the weight, the ambient temperature was maintained at 20° C.

The results of these tests are shown in Table 2.

COMPARATIVE EXAMPLE 1

Example 9 was repeated except that a commercial liquid resin A ("Wing Tack 10", a product of Goodyear Co.) as used instead of the novel substituted aromatic hydrocarbon of this invention.

COMPARATIVE EXAMPLE 2

Example 9 was repeated except that a commercial liquid resin A ("YS Resin PX-200", a product of Yasuhara Oils and Fats Co., Ltd.) was used instead of the novel substituted aromatic hydrocarbon of this invention.

COMPARATIVE EXAMPLE 3

Example 9 was repeated except that a commercial liquid resin B ("Dimeron", a product of Yasuhara Oils and Fats Co., Ltd.) was used instead of the novel substituted aromatic hydrocarbon of this invention.

The above results show that when the novel substituted aromatic hydrocarbons obtained by this invention are used as tackifiers for hot-melt type pressure-sensitive adhesives, the resulting adhesive compositions have better adhesive properties than those obtained by using the resins mentioned in Comparative Examples, and the balance between adhesive properties (corrugated cardboard adhesion and corrugated cardboard holding power), which is unsatisfactory in conventional adhesive compositions of this type, can be greatly improved.

EXAMPLES 15–20

One hundred parts by weight of SEBS block copolymer ("GX-1657", a product of Shell Chemical Co.), 57 parts by weight of a commercial hydrogenated petroleum resin "Arkon P-70", a product of Arakawa Chemical Co., Ltd.), 1 part by weight of a stabilizer ("Irganox 1010", a product of Ciba-Geigy), and 129 parts by weight of each of the resins obtained in Examples 1 to 6 as a tackifier were kneaded by a kneader at 150° C. for 30 minutes to prepare an adhesive.

An adhesive tape was prepared and evaluated in the same way as in Example 9. The results are shown in Table 3.

The compatibility of the substituted aromatic hydrocarbon with the other ingredients in the kneaded mixture was evaluated as follows: The adhesive was heat-melted and coated on a glass plate to a thickness of 2 to 3 mm. The compatibility was evaluated by the transparency of the adhesive on the following scale.

O: Good compatibility (transparent)
Δ: Slightly poor compatibility (semitransparent)
X: Poor compatibility (non-transparent)

COMPARATIVE EXAMPLE 4

Example 15 was repeated except that a commercial liquid resin A ("Wing Tack 10", a product of Goodyear Co.) was used instead of the novel substituted aromatic hydrocarbon of this invention.

COMPARATIVE EXAMPLE 5

Example 15 was repeated except that a commercial liquid resin D ("Polybutene-10H-T", a product of Idemitsu Petrochemical Co., Ltd.) was used instead of the novel substituted aromatic hydrocarbon of this invention.

COMPARATIVE EXAMPLE 6

Example 15 was repeated except that a commercial liquid resin E ("Kuraprene LIR-50", a product of Kurare Isoprene Chemical Co., Ltd.) was used instead of the novel substituted aromatic hydrocarbon of this invention.

TABLE 2

| Example (Ex.) or Comparative Example (CEx.) | Ex. 9 | Ex. 10 | Ex. 11 | Ex. 12 | Ex. 13 | Ex. 14 | CEx. 1 | CEx. 2 | CEx. 3 |
|---|---|---|---|---|---|---|---|---|---|
| Resin used | Ex. 1 | Ex. 2 | Ex. 3 | Ex. 4 | Ex. 5 | Ex. 6 | Resin A | Resin B | Resin C |
| Properties of the adhesive | | | | | | | | | |
| Corrugated cardboard adhesion (5° C.) | 4 | 5 | 5 | 5 | 4 | 4 | 2 | 2 | 2 |
| Tack at 20° C. (ball No.) | 13 | 15 | 14 | 15 | 14 | 13 | 9 | 12 | 13 |
| Adhesion strength at 20° C. (g/25 mm width) | 1300 | 1350 | 1400 | 1500 | 1400 | 1400 | 900 | 1000 | 1200 |
| Cohesive force at 20° C. (mm/2 HR) | 0.2 | 0.2 | 0.1 | 0.1 | 0.1 | 0.2 | 0.2 | 0.3 | 0.3 |
| Corrugated cardboard | 36 | 38 | 40 | 45 | 41 | 37 | 19 | 16 | 17 |

TABLE 2-continued

| Example (Ex.) or Comparative Example (CEx.) | Ex. 9 | Ex. 10 | Ex. 11 | Ex. 12 | Ex. 13 | Ex. 14 | CEx. 1 | CEx. 2 | CEx. 3 |
|---|---|---|---|---|---|---|---|---|---|
| holding power at 20° C. (HR) | | | | | | | | | |

TABLE 3

| Example (Ex.) or Comparative Example (CEx.) | Ex. 15 | Ex. 16 | Ex. 17 | Ex. 18 | Ex. 19 | Ex. 20 | CEx. 4 | CEx. 5 | CEx. 6 |
|---|---|---|---|---|---|---|---|---|---|
| Resin used | Ex. 1 | Ex. 2 | Ex. 3 | Ex. 4 | Ex. 5 | Ex. 6 | Resin A | Resin D | Resin E |
| Properties of the adhesive | | | | | | | | | |
| Compatibility | O | O | O | O | O | O | O | Δ | X |
| Tack at 20° C. (ball No.) | 4 | 5 | 7 | 8 | 6 | 5 | <2 | 8 | 13 |
| Adhesion strength at 20° C. (g/25 mm width) | 1000 | 1050 | 1150 | 1200 | 1100 | 1100 | 800 | 300 | 50 |
| Cohesive force at 20° C. (mm/2 HR) | 0.2 | 0.2 | 0.1 | 0.1 | 0.1 | 0.2 | 0.2 | * | * |
| Corrugated cardboard holding power at 20° C. (HR) | 27 | 28 | 32 | 37 | 34 | 31 | 13 | * | * |

(*): The weight and tape dropped immediately after the weight was suspended from the tape.

EXAMPLE 21

A 500 ml steel autoclave was charged with 34 g of tricyclo[5.2.1.0$^{2,6}$]dec-4-ylbenzene obtained in Example 1, 118 g of Mitsui Hexane (a product of Mitsui Petrochemical Co., Ltd.) and 2.5 g of a sulfur-resistant nickel catalyst ("N-1138", a product of Nikki Chemical Co., Ltd.) as a hydrogenation catalyst, and hydrogenation was carried out at 200° C. and 40 kg/cm$^2$-G for 5 hours. After cooling, pressure releasing and nitrogen purging, the catalyst was separated by filtration. The filtrate was distilld to obtain 33 g of a colorless distillate at a column top temperature of 144° to 150° C. and a pressure of 7 mmHg. The product was determined from its molecular weight of 218 (theory 218) and its infrared absoprtion spectrum (shown in FIG. 3) to be tricyclo[5.2.1.0$^{2,6}$]-dec-4-yl-cyclohexane. The refractive index ($n_D^{25}$) was 1.5110.

Figure 3:
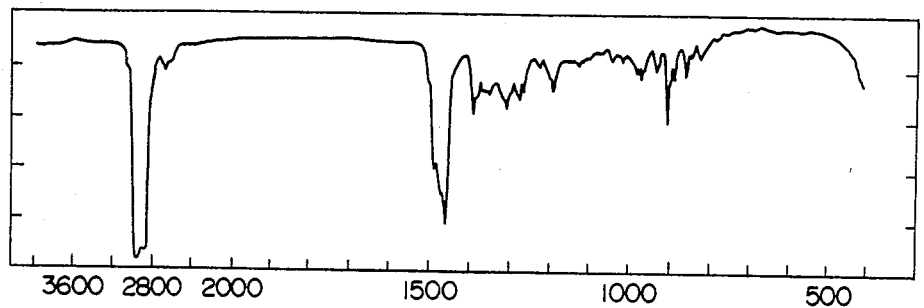

FIG. 3 shows the infrared absorption spectrum of the reaction product obtained in Example 21 with wave numbers plotted on the abscissa.

EXAMPLE 22

Eighty grams of the mixture of 2-, 3- and 4-tricyclo[5.2.1.0$^{2,6}$]dec-4-yltoluene obtained in Example 2 was hydrogenated under the conditions shown in Table 4 by the same operation as in Example 21. After the hydrogenation, the catalyst was separated by filtration, and the filtrate was distilled at a column top temperature of 154° to 158° C. and a pressure of 7 mmHg to give 78 g of a colorless distillate. From its molecular weight of 232 (theory 232) and other data, the product was determined to be a mixture of 2-, 3- and 4-tricyclo[5.2.1.0$^{2,6}$]dec-4-ylmethylcyclohexanes.

The refractive index ($n_D^{25}$) was 1.5080.

EXAMPLE 23

The mixture of 2-, 3- and 4-tricyclo[5.2.1.0$^{2,6}$]dec-4-ylethylbenzenes obtained in Example 3 was hydrogenated under the conditions shown in Table 4 by the same operation as in Example 21. After hydrogenation, the catalyst was separated by filtration, and the filtrate was distilled at a column top temperature of 163° to 168° C. and a pressure of 7 mmHg to obtain 98 g of a colorless distillate. From its molecular weight of 246 (theory 246) and other data, the product was determined to consist mainly of a mixture of 2-, 3- and 4-tricyclo[5.2.1.0$^{2,6}$]dec-4-ylethylcyclohexanes.

EXAMPLE 24

The mixture consisting of 1:1 adduct of tricyclo[5.2.1.0$^{2,6}$]dec-3-ene/mixed xylene adduct, 33% by weight of 2:1 tricyclo[5.2.1.0$^{2,6}$]dec-3-ene/mixed xylene adduct and 8% by weight of other components which was obtained in Example 4 was hydrogenated under the conditions shown in Table 4 by the same operation as in Example 1. After the hydrogenation, the catalyst was separated by filtration, and the filtrate was heated at a reactor temperature of 150° C. and a pressure of 20 mmHg to remove the solvent. There was obtained 39 g of a viscous liquid having a viscosity of 10600 cps at 25° C. and a refractive index ($n_D^{25}$) of 1.5028.

Analysis showed it to be composed of 59% by weight of the hydrogenated 1:1 tricyclo[5.2.1.0$^{2,6}$]dec-3-ene/-mixed xylene adduct, 33% by weight of the hydrogenated 2:1 tricyclo[5.2.1.0$^{2,6}$]dec-3-ene/mixed xylene adduct, and 8% by weight of other components.

EXAMPLES 25–26

The same reaction as in Example 24 was carried out under the conditions shown in Table 4. The unreacted materials were removed, and the amounts and properties of the reaction products are shown in Table 5.

EXAMPLE 26

One hundred parts by weight of SEBS block copolymer ("G-1657", a product of Shell Chemical Co.), 57 parts by weight of a commercial hydrogenated petroleum resin ("Arkon P-70", a product of Arakawa Chemical Co., Ltd.), 1 part by weight of a stabilizer ("Irganox 1010", a product of Ciba-Geigy), and 129 parts by weight of each of the resins obtained in Examples 21 to 26 as a tackifier were kneaded by a kneader at 150° C. for 30 minutes to prepare an adhesive. The adhesive was heat-melted (for 20 minutes) on a polyester film (thickness 25 microns) on a hot plate kept at 195° C., and coated to a thickness of 30±5 microns by using an applicator to prepare an adhesive tape.

The adhesives were evaluated by the testing methods described hereinabove, and the results are shown in Table 6.

The above results show that when the novel hydrogenated substituted aromatic hydrocarbons obtained by this invention are used as softening agents for hot-melt type pressure-sensitive adhesives, the resulting adhesive compositions have better adhesive properties than those obtained by using the compounds obtained in Comparative Examples 4 to 6.

TABLE 4

| | Example | | | | | |
|---|---|---|---|---|---|---|
| | 21 | 22 | 23 | 24 | 25 | 26 |
| Hydrogenation conditions | | | | | | |
| Substituted aromatic hydrocarbon | Example 1 | Example 2 | Example 3 | Example 4 | Example 5 | Example 6 |
| Amount of the substituted aromatic hydrocarbon (g) | 34 | 80 | 100 | 40 | 60 | 60 |
| Amount of the solvent (MITSUI HEXANE) (g) | 118 | 195 | 200 | 139 | 209 | 209 |
| Amount of the sulfur-resistant nickel catalyst (g) | 2.5 | 5.8 | 7.3 | 2.9 | 4.4 | 4.4 |
| Temperature (°C.) | 200 | 200 | 200 | 200 | 200 | 200 |
| Time (hours) | 5 | 5 | 5 | 5 | 5 | 5 |
| Pressure (kg/cm$^2$) | 40 | 40 | 40 | 40 | 40 | 40 |
| Amount of the hydrogenated product (g) | 33 | 78 | 98 | 39 | 59 | 59 |

TABLE 5

| Example | 4 | 5 | 6 |
|---|---|---|---|
| Softening point (°C.) | <5 | 10.8 | 22.5 |
| Viscosity (cps/25° C.) | 10,600 | 40,000 | 56,900 |
| Gardner color number | <1 | <1 | <1 |
| Content of the 1:1 product (wt. %) | 59 | 37 | 33 |

TABLE 6

| Example (Ex.) or Comparative Example (CEx.) | Ex. 27 | Ex. 28 | Ex. 29 | Ex. 30 | Ex. 31 | Ex. 32 | CEx. 4 | CEx. 5 | CEx. 6 |
|---|---|---|---|---|---|---|---|---|---|
| Hydrogenated substituted aromatic hydrocarbon | Ex. 21 | Ex. 22 | Ex. 23 | Ex. 24 | Ex. 25 | Ex. 26 | Resin A | Resin D | Resin E |
| Compatibility | O | O | O | O | O | O | O | Δ | X |
| Tack at 20° C. (ball No.) | 6 | 7 | 8 | 9 | 7 | 6 | <2 | 8 | 13 |
| Adhesion strength at 20° C. (g/25 mm width) | 1000 | 1000 | 1100 | 1100 | 1050 | 1050 | 800 | 300 | 50 |
| Cohesive force at 20° C.) (mm/2 HR) | 0.2 | 0.2 | 0.1 | 0.1 | 0.1 | 0.2 | 0.2 | * | * |

(*): The same as the footnote to Table 3.

EXAMPLE 33

Figure 4:
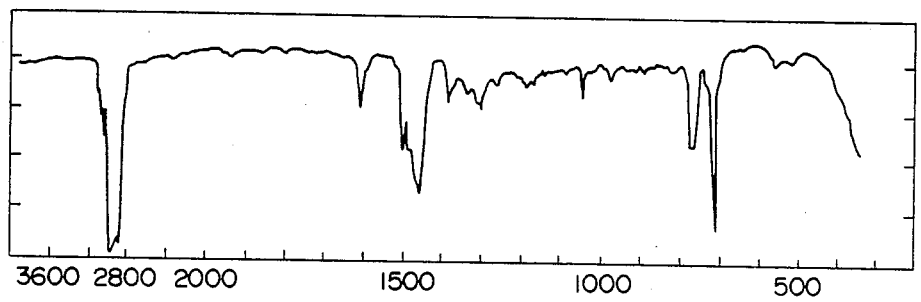
Figure 5:
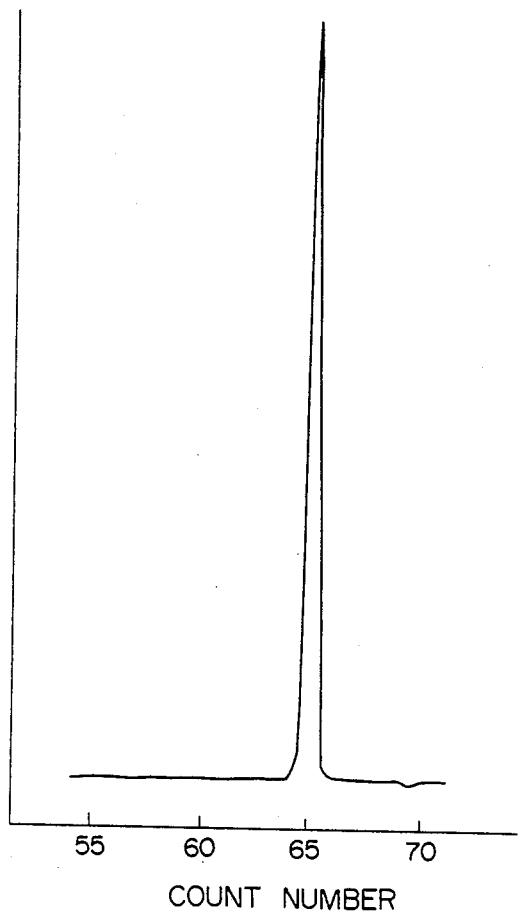

A 500 ml four-necked flask equipped with a thermometer, a stirrer and a condenser was charged with 195 g (2.5 moles) of benzene and 1.0 g of AlCl$_3$ powder in an atmosphere of nitrogen. With stirring, 78 g (0.5 mole) of 9-methyl-tetracyclo[6.2.1.1$^{3,6}$.0$^{2,7}$]-4-dodecene was added dropwise at 60° C. for about 30 minutes. The reaction was then continued for 1.5 hours at 60° C. The catalyst was then decomposed with methanol, and the reaction mixture was washed with water. The unreacted materials were removed by distillation. The residue was distilled under reduced pressure to give 15.0 g of a colorless fraction having a boiling point of 182° to 184° C./5 mmHg (n$_D^{25}$=1.4940). The product was found to be 9-methyl-tetracyclo[6.2.1.1$^{3,6}$.0$^{2,7}$]dodeca-3(or 4)-ylbenzene from its molecular weight of 252 (theory 252) and the absorptions of mono-substituted benzene at 760 and 705 cm$^{-1}$ in its infrared absorption spectrum (FIG. 4). The gel permeation chromatogram of this product is shown in FIG. 5.

FIG. 4 is the infrared absorption spectrum of the reaction product obtained in Example 33 with wave numbers plotted on the abscissa. FIG. 5 is the gel permeation chromatogram of the reaction product obtained in Example 33 with count numbers plotted on the abscissa.

EXAMPLE 34

Toluene (50 g) and 1.3 g of AlCl$_3$ powder were taken into the same flask as used in Example 33 in an atmosphere of nitrogen and stirred. 102 g of 9-methyl-tetracyclo[6.2.1$^{3,6}$.0$^{2,7}$]-4-dodecene, 70.5 g of toluene and 10 g of n-decane were added dropwise through a dropping funnel for about 30 minutes while maintaining a reaction temperature of 60° C. The reaction was continued at 60° C. for 1.5 hours. Gas chromatographic analysis of the reaction mixutre at this time showed that 100% of 9-methyl-tetracyclo[6.2.1.1$^{3,6}$.0$^{2,7}$]-4-dodecene and 31% of toluene were reacted. The reaction mixture was washed with water and concentrated to give 140 g of a liquid resin (n$_D^{25}$=1.5591). Gel permeation chromatography of the liquid resin showed that it consisted of 73.5% of toluene monosubstituted by 9-methyl-tetracyclo[6.2.1.1$^{3,6}$.0$^{2,7}$]-4-dodecenyl, 13.6% of toluene disubstituted by 9-methyl-tetracyclo[6.2.1.1$^{3,6}$.0$^{2,7}$]-4-dodecenyl, 1.9% of a dimer of 9-methyltetracyclo[6.2.1$^{3,6}$.0$^{2,7}$]-4-dodecene, and 11.0 parts of a high-molecular-weight product.

Figure 6:
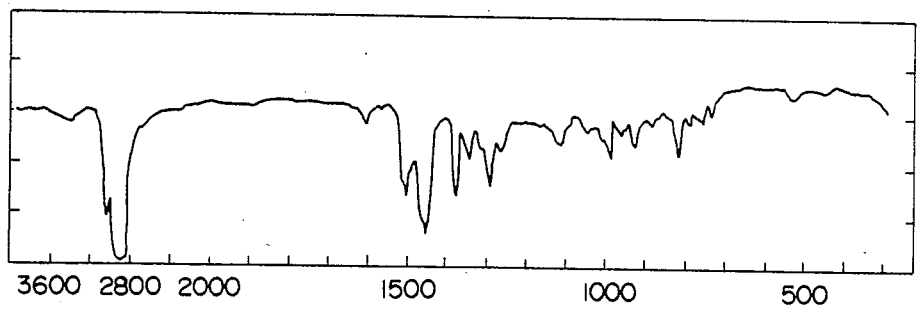
Figure 8:
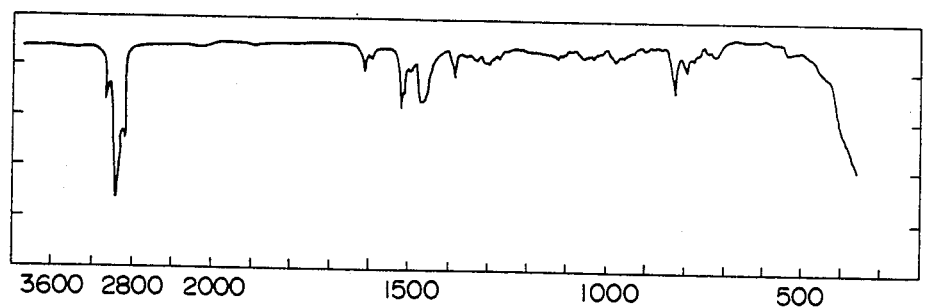

The infrared absorption spectrum of the resulting liquid resin is shown in FIG. 6. FIGS. 4, 6 and 8 respectively show the infrared absorption spectra of the reaction products obtained in Examples 33, 34 and 36 in which the abscissas represent wave numbers.

Figure 7:
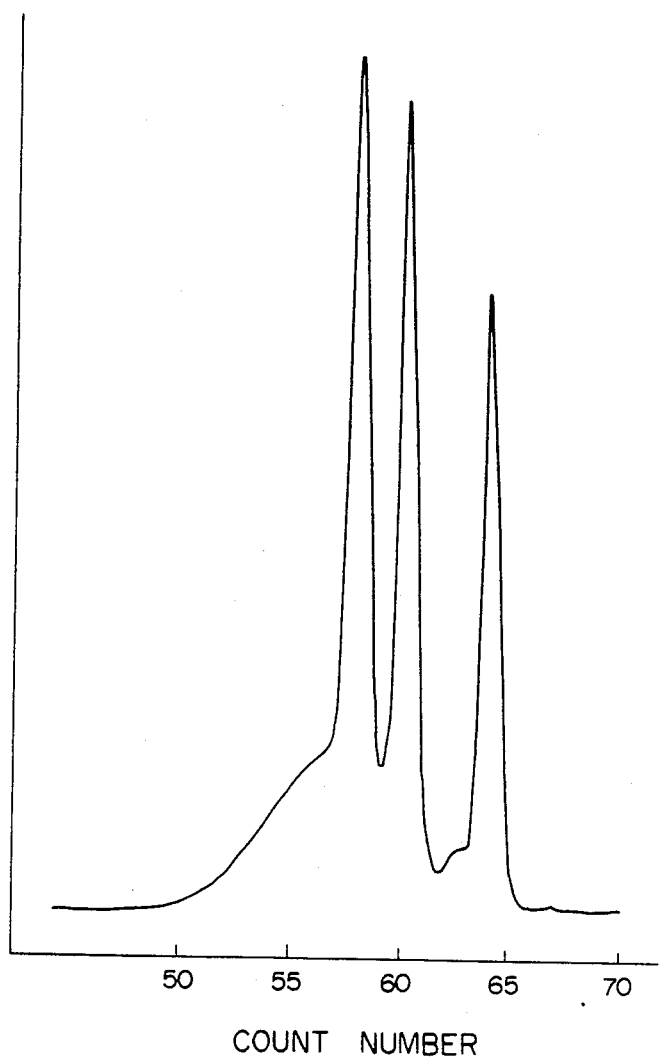

FIGS. 5 and 7 show gel-permeation chromatograms of the products obtained in Examples 33 and 35 in which the abscissas represent count numbers.

EXAMPLE 35

Toluene (65 g), 65 g of n-decane and 2.7 g of AlCl$_3$ powder were taken into the same flask as used in Example 33 in an atmosphere of nitrogen, and stirred. One hundred grams of 9-methyltetracyclo[6.2.1.1$^{3,6}$.0$^{2,7}$]-4-dodecene was added dropwise through a dropping funnel for about 30 minutes while maintaining a reaction temperature of 60° C. The reaction was continued at 60° C. for 1.5 hours. The reaction mixture was washed with water and concentrated to give a solid resin having a softening point of 90° C. and a Gardner color number of 6.5. It had a number molecular weight ($\overline{Mn}$) of 354. The $\overline{Mw}/\overline{Mn}$ ratio was 1.2.

Gel permeation chromatography of the resulting resin showed that it consisted of 19.6% of toluene mono-substituted by 9-methyltetracyclo[6.2.1.1$^{3,6}$.0$^{2,7}$]-4-dodecenyl, 29.4% of toluene disubstituted by 9-methyltetracyclo[6.2.1.1$^{3,6}$.0$^{2,7}$]-4-dodecenyl, 32.5% of toluene trisubstituted by 9-methyltetracyclo[6.2.1.1$^{3,6}$.0$^{2,7}$]-4-dodecenyl, and 2.2% of a dimer of 9-methyltetracyclo[6.2.1.1$^{3,6}$.0$^{2,7}$]-4-dodecene. The gel permeation chromatogram of the solid resin is shown in FIG. 7 in which the abscissa represents count numbers.

EXAMPLE 36

Toluene (115 g; 1.25 moles) and 0.5 g of AlCl$_3$ powder were stirred in the same four-necked flask as used in Example 33 in an atmosphere of nitrogen, and 47.5 g (0.25 mole) of 9-ethyltetracyclo[6.2.1.1$^{3,6}$.0$^{2,7}$]-4-dodecene was added dropwise through a dropping funnel for about 30 minutes while maintaining a reaction temperature of 60° C. The reaction was continued for 1.5 hours at 60° C. The catalyst was decomposed with methanol, and the reaction mixture was washed with water, and concentrated with stirring at 230° C. and 2 mmHg to remove the unreacted monomers. Thus, 69.1 g of a liquid resin (n$_D$$^{25}$=1.5461) was obtained. Gel permeation chromatographic analysis of the liquid resin showed that it consisted of 92.5% of toluene monosubstituted by 9-ethyltetracyclo[6.2.1.1$^{3,6}$.0$^{2,7}$]-4-dodecenyl, 6.0% of toluene disubstituted by 9-ethyltetracyclo[6.2.1.1$^{3,6}$.0$^{2,7}$]-4-dodecenyl, and 1.5% of other components.

The infrared absorption spectrum of this liquid resin is shown in FIG. 8.

COMPARATIVE EXAMPLE 7

Toluene (113 g), 10 g of n-heptane and 1.3 g of AlCl$_3$ powder were taken into the same flask as used in Example 33 in an atmosphere of nitrogen, and stirred. One hundred grams of 5-methylnorbornene was added dropwise through a dropping funnel while maintaining a reaction temperature of 60° C. The reaction was continued at 60° C. for 1.5 hours. Gas chromatographic analysis of the reaction mixture at this time showed that 42% of 5-methyl-norbornene and 14% of toluene reacted. The reaction mixture was washed with water to remove the unreacted monomers to obtain 58 g of a liquid resin having a strong odor. The resin had a Gardner color number of 9. Analysis of the resin by liquid chromatography showed that it consisted of 55% of toluene mono-substituted by 5-methyl-norbornene, 21% of toluene disubstituted by 5-methyl-norbornene and 18% of a high-molecular-weight component.

EXAMPLES 37-39 AND COMPARATIVE EXAMPLE 8

One hundred parts by weight of SIS block copolymer ("Kraiton TR-1107", a product of Shell Chemical Co.), 30 parts of a softening agent ("Shellflex 22R", a product of Shell Chemical Co., 3 parts by weight of a stabilizer ("Irganox 1010", a product of Ciba-Geigy), 70 parts by weight of a commercial aliphatic petroleum resin ("Hi-rez T-300X", a product of Mitsui Petrochemical Industries, Ltd.) and 30 parts by weight of each of the liquid resins obtained in Examples 33, 34 and 36 and Comparative Example 7 as a tackifier were kneaded by a kneader at 150° C. for 30 minutes to prepare an adhesive. The adhesive was heat-melted (for 20 minutes) on a polyester film (thickness 25 microns) on a hot plate kept at 195° C., and coated to a thickness of 30±5 microns by using an applicator to prepare an adhesive tape.

The properties of the adhesive were evaluated by the same testing methods as in Example 9. The results are shown in Table 7.

TABLE 7

| Example (Ex.) or Comparative Example (CEx.) | Ex. 37 | Ex. 38 | Ex. 39 | CEx. 8 | CEx. 3 | CEx. 4 |
|---|---|---|---|---|---|---|
| Resin used | Ex. 33 | Ex. 34 | Ex. 36 | CEx. 7 | Resin A | Resin B |
| Properties of the adhesive | | | | | | |
| Corrugated cardboard adhesion (5° C.) | 4 | 4 | 4 | 2 | 2 | 2 |
| Tack at 20° C. (ball No.) | 14 | 14 | 14 | 8 | 9 | 12 |
| Adhesion strength at 20° C. (g/25 mm width) | 1300 | 1500 | 1400 | 900 | 900 | 1000 |
| Cohesive force at 20° C. (mm/2 HR) | 0.2 | 0.1 | 0.2 | 0.3 | 0.2 | 0.3 |
| Corrugated cardboard holding power at 20° C. (HR) | 35 | 45 | 38 | 15 | 19 | 16 |

EXAMPLE 40

Example 37 was repeated except that 100 parts by weight of the SIS block copolymer ("TR-1107", a product of Shell Chemical Co.), 30 parts by weight of the softening agent ("Shellflex 22R", a product of Shell Chemical Co., 3 parts by weight of the stabilizert ("Irganox 1010", a product of Ciba-Geigy) and 100 parts of the resin obtained in Example 35 were blended and formed into an adhesive.

COMPARATIVE EXAMPLE 9

Example 40 was repeated except that "Hi-rez T-300X" (a product of Mitsui Petrochemical Industries, Ltd.) was used instead of the novel substituted aromatic hydrocarbon of this invention.

COMPARATIVE EXAMPLE 10

Example 40 was repeated except that a commercial product C ("Wing Tack", a product of Goodyear Co.)

as used instead of the novel substituted aromatic hydrocarbon of this invention.

The results obtained in Example 40 and Comparative Examples 9 and 10 are shown in Table 8.

TABLE 8

| Resin used | Example (Ex.) or Comparative Example (CEx.) | | |
|---|---|---|---|
| | Ex. 40 Ex. 35 | CEx. 9 Hi-rez T-300X | CEx. 10 Commercial resin C |
| Properties of the adhesive | | | |
| Corrugated cardboard adhesion (5° C.) | 4 | 2 | 2 |
| Tack at 20° C. (ball No.) | 15 | 11 | 9 |
| Adhesion strength at 20° C. (g/25 mm width) | 1500 | 1500 | 1700 |
| Cohesive force at 20° C. (mm/2 HR) | 0.1 | 0.2 | 0.2 |
| Corrugated cardboard holding power at 20° C. (HR) | 70 | 40 | 20 |

The above results show that when the novel substituted aromatic hydrocarbons obtained by this invention are used as tackifiers for hot-melt type pressure-sensitive adhesives, the resulting adhesive compositions have better adhesive properties than those obtained by using the resins mentioned in Comparative Examples, and the balance between adhesive properties (corrugated cardboard adhesion and corrugated cardboard holding power), which is unsatisfactory in conventional adhesive compositions of this type, can be greatly improved.

EXAMPLE 41

A 500 ml four-necked flask equipped with a thermometer, a stirrer, a condenser and a catalyst introducing rubber cap was charged with 9.4 g (0.1 mole) of phenol and 92.1 g (0.6 mole) of a fraction containing tricyclo[5.2.1.0$^{2,6}$]dec-3-ene (purity 87.3%) in an atmosphere of nitrogen. The compounds were stirred at room temperature to dissolve them uniformly. Eight grams of a $BF_3$-phenol complex ($BF_3$ content 30% by weight) was slowly added dropwise through the rubber cap by using an injection syringe. The mixture was reacted at 60° C. A 10% aqueous solution of sodium carbonate was added to the reaction mixture to stop the reaction. The reaction mixture was diluted with toluene and washed with warm water until it became neutral. It was concentrated at 210° C. and 10 mmHg to give 88 g of a reddish brown resinous product.

The reaction product had a number average molecular weight (vapor pressure method) of 500 (theory 502) and an oxygen content, found by elemental analysis, of 3.1% (calculated 3.22%). From these data and its infrared absorption spectrum, the product was determined to have 2,4,6-tri(tricyclo[5.2.1.0$^{2,6}$]dec-3-(or 4)-yl)phenol as a main component.

The product was found to have a softening point (measured by a ring and ball method in accordance with JIS K-2531) of 105° C. and a melt viscosity (measured by an Emila-type rotary viscometer) of 70 centipoises (200° C.).

Figure 9:
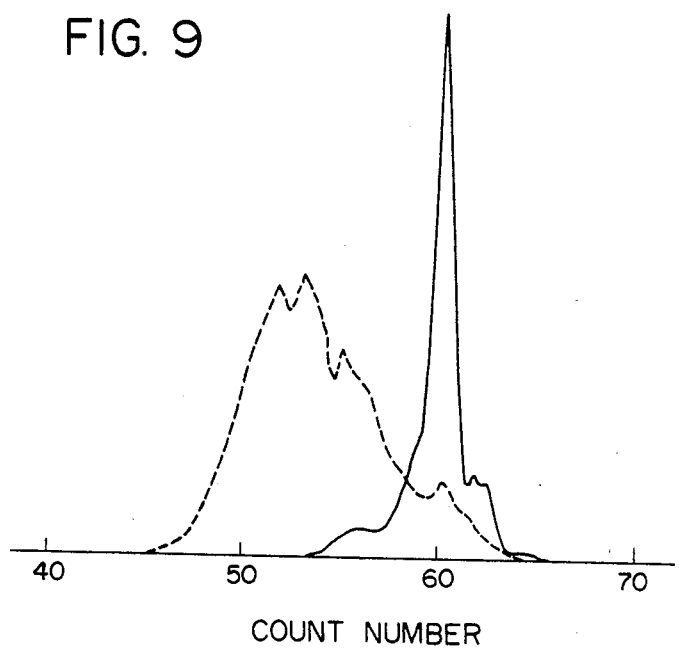

The gel permeation chromatogram of the product is shown in FIG. 9 (the solid line). FIG. 9 also shows the gel permeation chromatogram of a commercial terpene-phenol resin (YS Polyster T-115, a product of Yasuhara Oils and Fats Co., Ltd.; $\overline{Mn}$ by the vapor pressure method 600, $\overline{Mw}/\overline{Mn}$=1.52, softening point 115° C.) by the dotted line. By comparison with the latter, it is clear that the reaction product ($\overline{Mw}/\overline{Mn}$=1.04) obtained in the present Example was nearly monodisperse.

EXAMPLE 42

Example 41 was repeated except that 10.8 g (0.1 mole) of p-cresol was used instead of phenol, 6.2 g of $BF_3$-ether complex was used as the catalyst, the fraction containing tricyclo[5.2.1.0$^{2,6}$]-dec-3-ene was used in an amount of 62.3 g (0.4 mole), and the reaction time was changed to 5 hours. As a result, 26.5 g of a brown resinous product was obtained.

The resulting product was found to have a number average molecular weight of 380 (theory 377) and an oxygen content, measured by elemental analysis, of 4.2% (calculated 4.25%). From these data and its infrared absorption spectrum, the product was determined to contain 4-methyl-2,6-di(tricyclo[5.2.1.0$^{2,6}$]dec-3 (or 4)-yl)phenol as a main component.

The product also had a softening point of 82° C. and a melt viscosity of 20 centipoises (200° C.). In gel permeation chromatography, the product was found to have an $\overline{Mw}/\overline{Mn}$ ratio of 1.04.

EXAMPLE 43

In the procedure of Example 41, 41.68 g (0.2 mole) of bisphenol A was used instead of phenol, 16.3 g of a $BF_3$-ether was used as the catalyst, and 303.5 g (1.6 mole) of a fraction containing tricyclo[5.2.1.0$^{2,6}$]dec-3-ene (purity 70.64%) was used. The reaction was carried out at 60° C. for 4 hours. The catalyst was then decomposed with a 10% aqueous solution of sodium hydroxide, and the reaction mixture was acidified with 10% hydrochloric acid, washed with water, and concentrated to give 140 g of a brown resinous product.

The reaction product was found to have a number average molecular weight of 700 (theory 765) and an oxygen content, by elemental analysis, of 3.7% (calculated 4.18%). From these data and its infrared absorption spectrum (3200-3600 cm$^{-1}$ assigned to the OH group), it was determined to contain 2,2-bis{4-hydroxy-3,5-di(tricyclo[5.2.1.0$^{2,6}$]dec-3 (or 4)-yl)phenyl}propane as a main component.

The product also had a softening point of 102° C. and a melt viscosity of 90 centipoises (200° C.). In gel permeation chromatography, the product had an $\overline{Mw}/\overline{Mn}$ ratio of 1.15.

EXAMPLES 44-46 AND COMPARATIVE EXAMPLES 11-12

One hundred parts by weight of a styrene/isoprene/styrene block copolymer rubber (Kraiton TR-1107, a product of Shell Chemical Co.), 100 parts by weight of each of the resins shown in Table 9 below, 30 parts by weight of a softening agent ("Shellflex 22R", a product of Shell Chemical Co.) and 3 parts by weight of a stabilizer ("Irganox 1010", a product of Ciba-Geigy) were kneaded at 150° C. for 30 minutes by a kneader to prepare an adhesive. The adhesive was coated under heat on a polyester film (Lumilar, a product of Toray Inc.; thickness 25 microns) to a thickness of 30 microns.

The tack of the adhesive was measured by the J. Dow method at 20° C., and its adhesion strength and holding power were measured at 20° C. by the method of JIS Z-1524. The results are shown in Table 9.

TABLE 9

| Example | Resin or resinous product | Tack (ball No.) | Adhesion strength (g/25 mm width) | Holding power (mm) |
|---|---|---|---|---|
| Ex. 44 | Resinous product obtained in Example 41 | 12 | 2450 | 0.2 |
| Ex. 45 | Resinous product obtained in Example 42 | 10 | 2080 | 0.2 |
| Ex. 46 | Resinous product obtained in Example 43 | 11 | 2860 | 0.1 |
| CEx. 11 | Commercial terpene-phenol resin (YS Polyster T-115, a product of Yasuhara Oils and Fats Co., Ltd.) | 10 | 1840 | 0.2 |
| CEx. 12 | Commercial terpene-bisphenol A resin (YS Polyster-2130, a product of Yasuhara Oils and Fats Co., Ltd.) | 4 | 1920 | 0.1 |

EXAMPLE 47 AND COMPARATIVE EXAMPLE 13

Eighty parts by weight of the resinous reaction product obtained in Example 41 and 50 parts by weight each of two ethylene/vinyl acetate copolymers (Evaflex 220 and 250, products of Mitsui Polychemical Co., Ltd.) were mixed under heat in the molten state to prepare a hot-melt adhesive. The hot-melt adhesive (melt viscosity 4500 centipoises, 180° C.) was melted and coated on aluminum substrates each having a thickness of 50 microns to a thickness of 15 microns. The coated surfaces were heat-sealed at 170° C. and 1 kg/cm$^2$ for 2 seconds. The peel strength of the bonded product was measured by the T-peel method at various temperatures. The results are shown in Table 10. As Comparative Example 13, the peel strength of a commercial hot-melt adhesive ("Bind-quick", a product of Horizon Co.) is also shown in Table 10.

TABLE 10

| Hot-melt adhesive | Peel strength (g/25 mm width) | | |
|---|---|---|---|
| | 0° C. | 25° C. | 45° C. |
| Example 47 | 1250 | 1800 | 1010 |
| Comparative Example 43 | 980 | 1450 | 320 |

EXAMPLE 48

In the procedure of Example 41, 12.2 g (0.1 mole) of 2,6-xylenol was used instead of phenol, 6.7 g of BF$_3$-ether complex was used as the catalyst, and the fraction containing tricyclo[5.2.1.0$^{2,6}$]-dec-3-ene was used in an amount of 62.3 g (0.4 mole). The reaction was carried out at 70° C. for 4 hours. The catalyst was decomposed with a 10% aqueous solution of sodium hydroxide. The reaction mixture was acidified with 10% hydrochloric acid, washed with water and concentrated. As a result, 18.5 g of a fraction having a boiling point of 172 to 179° C./2 mmHg was obtained. Recrystallization from chloroform gave 12.4 g of white crystals having a melting point of 126 to 128° C.

The reaction product was determined to be 2,6-dimethyl-4-(tricyclo[5.2.1.0$^{2,6}$]dec-3(or 4)-yl)phenol from its mass spectrum data (M/e:256) and elemental analysis values [C 84.3% (calculated 84.32%) and H 9.4% (calculated 9.44%)] and its infrared absorption spectrum.

EXAMPLE 49 AND COMPARATIVE EXAMPLES 14–16

One hundred parts by weight of alkylstyrene resin containing no stabilizer (FTR-6100, a product of Mitsui Petrochemical Industries, Ltd.) and 0.1 part by weight of the reaction product obtained in Example 48 were fed into a test tube having an inside diameter of 16 mm and a length of 180 mm, and well mixed by a spatula in an oil bath at 200° C. Changes in the color hue of the mixture on the oil bath were evaluated by Gardner color numbers. The results are shown in Table 11.

For comparison; The above procedure was repeated without adding the reaction product of Example 48, or using general stabilizers. The results are also shown in Table 11.

TABLE 11

| Ex. CEx. | Additive | Heating time (hours) | | | | | |
|---|---|---|---|---|---|---|---|
| | | 0 | 4 | 8 | 12 | 16 | 20 |
| CEx. 14 | None | 1 | 3 | 5 | 7–8 | 8 | 9 |
| Ex. 49 | Reaction product of Example 48 | 1 | 1–2 | 2–3 | 3–4 | 4–5 | 5–6 |
| CEx. 15 | Butylated hydroxytoluene | 1 | 1–2 | 3 | 5 | 6–7 | 8 |
| CEx. 16 | Irganox 1076 D (*) | 1 | 2 | 3 | 4 | 5 | 6 |

(*): n-Octadecyl-3-(4'-hydroxy-3',5'-ditertbutyl phenol)propionate.

EXAMPLE 50

A 500 ml four-necked flask equipped with a stirrer, a thermometer and a dropping funnel was charged with 8.98 g of phenol and 0.62 g of BF$_3$-phenol complex (BF$_3$ content 30% by weight). The total amount of phenol was 0.1 mole. With stirring in an atmosphere of nitrogen, a mixture of 52.3 g (0.3 mole) of 9-methyl-tetracyclo[6.2.1.1.0$^{2,7}$]-4-dodecene, 42.3 g of hexane and 10 g of n-dodecane was added dropwise through the dropping funnel for 25 hours while maintaining a reaction temperature of 45° C. Two hours later, the reaction mixture was analyzed by gas chromatography. The conversion of 9-methyl-tetracyclo[6,2,1,1,0$^{2,7}$]-4-dodecene was 86%, and the conversion of phenol was 100%.

The catalyst was decomposed by adding 8.2 cc of a 1N aqueous NaOH solution. The reaction mixture was acidified with 20 cc of 1N HCl, and washed with water until it became neutral. The resin solution was concentrated at an oil temperature of 210° C. and a pressure of 10 mmHg for 15 minutes to give 59.4 g of a yellow solid resin. From its molecular weight (field desorption ionization mass analysis) of 616 (theory 616) and its infrared absorption spectral data, the resin was determined to contain 2,4,6-tri(9-methyl-tetracyclo[6.2.1.1.0$^{2,7}$]dodec-3 (or 4)-yl)phenol as a main component. The resin also had a softening point (ring-and-ball method JIS K-2531) of 128° C. melt viscosity (Emila-type rotary viscometer) of 210 centipoises (200° C.) and a Gardner color number of 11.

Figure 10:
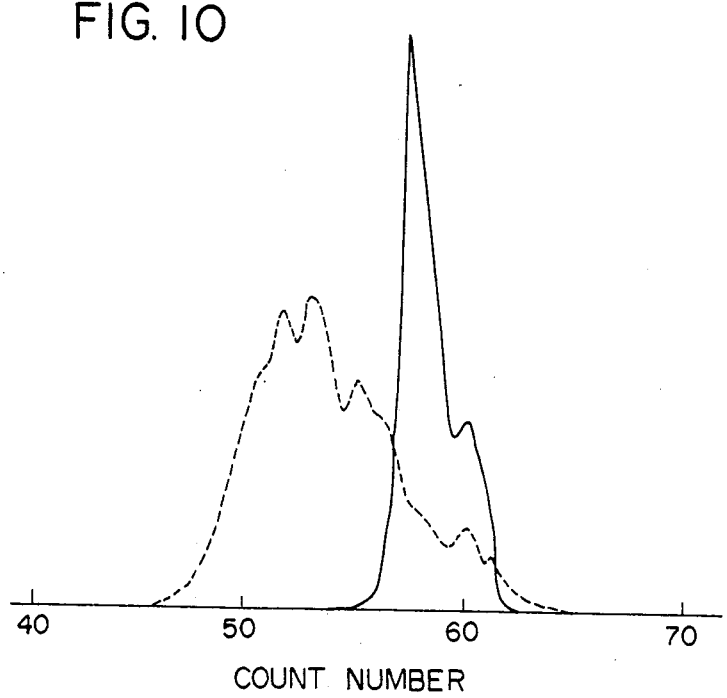

The gel permeation chromatogram of the resin is shown by the solid line in FIG. 10. FIG. 10 also shows the gel permeation chromatogram of a commercial terpene-phenol resin (YS Polyster T115, a product of Yasuhara Oils and Fats Co., Ltd.1; number average molecular weight by the vapor pressure method 600;

$\overline{M}w/\overline{M}n$-1.52; softening point 115° C.). By comparison with the latter, it is clear that the reaction product of this Example ($\overline{M}w/\overline{M}n$=108) is nearly monodisperse.

EXAMPLE 51

Example 50 was repeated except that 50, 21.63 g (0.2 mole) of p-cresol was used instead of phenol, 1.6 g of BF$_3$-ether complex was used as the catalyst, and 69.71 g (0.4 mole) of 9-methyltetracyclo[6.2.1.1.0$^{2,7}$]-4-dodecene, 59.7 g of hexane and 10 g of n-dodecane were used. There was obtained 84.8 g of a pale yellow solid resin. From its molecular weight of 282 (theory 282) and its infrared absorption spectral data, the resin was determined to contain 4-methyl-2 (or 3)-(9-methyl[6.2.1.1.0$^{2,7}$]dodec-3(or 4)-yl)phenol as a main component. The resin also had a softening point of 71.5° C., a melt viscosity of 8 centipoises (200° C.), a Gardner color number of 7 and an $\overline{M}w/\overline{M}n$ ratio (by gel permeation chromatography) of 1.07.

EXAMPLE 52

In the procedure of Example 50, 24.4 g (0.2 mole) of 2,6-xylenol was used instead of phenol, 1.5 g of BF$_3$-ether complex was used as the catalyst, and 52.31 g (0.3 mole) of 9-methyltetracyclo[6.2.1.1.0$^{2,7}$]-4-dodecene, 50 g of hexane and 10.0 g of n-dodecane were used. The reaction was carried out at 60° C. for 4 hours. Gas chromatographic analysis of the reaction mixture at this time showed that the conversion of bisphenol A was 100% and the conversion of 9-methyl-tetracyclododecene-4 was 90%. The catalyst was decomposed with a 1N aqueous sodium hydroxide solution. The reaction mixture was acidified with 1N HCl, washed with water and concentrated to give 89.0 g of a yellow solid resin. From its number average molecular weight (by the vapor pressure method) of 900 (theory 924) and its infrared absorption spectral data, the resin was determined to contain 2,2-bis{4-hydroxy-3,5-di(9-methyltetracyclo[6.2.1.1.0$^{2,7}$]dodec-3-(or 4)-yl)phenyl}propane as a main component. The resin also had a softening point of 145° C., a melt viscosity of 410 centipoises (200° C.), a Gardner color number of 10 and an $\overline{M}w/\overline{M}n$ ratio (by gel permeation chromatography) of 1.05.

EXAMPLES 54–57

One hundred parts by weight of a styrene/isoprene/styrene block copolymer rubber (Kraiton TR-1107, a product of Shell Chemical Co.), 100 parts by weight of each of the resins shown in Table 12 below, 30 parts by weight of a softening agent ("Shellflex 22R", a product of Shell Chemical Co.) and 3 parts by weight of a stabilizer ("Irganox 1010", a product of Ciba-Geigy) were kneaded at 150° C. for 30 minutes by a kneader to prepare an adhesive. The adhesive was coated under heat on a polyester film (Lumilar, a product of Toray Inc.; thickness 25 microns) to a thickness of 30 microns.

The tack of the adhesive was measured by the J. Dow method at 20° C., and its adhesion strength and holding power were measured at 20° C. by the method of JIS Z-1524. The results are shown in Table 12.

TABLE 12

| Example | Resin or resinous product | Tack (ball No.) | Adhesion strength (g/25 mm width) | Holding power (mm) |
| --- | --- | --- | --- | --- |
| 54 | Resinous product | 13 | 2500 | 0.1 |

TABLE 12-continued

| Example | Resin or resinous product | Tack (ball No.) | Adhesion strength (g/25 mm width) | Holding power (mm) |
| --- | --- | --- | --- | --- |
|  | obtained in Example 50 |  |  |  |
| 55 | Resinous product obtained in Example 51 | 14 | 1950 | 0.2 |
| 56 | Resinous product obtained in Example 52 | 13 | 2010 | 0.1 |
| 57 | Resinous product obtained in Example 53 | 11 | 2850 | 0.1 |

EXAMPLE 58

Eighty parts by weight of the resinous reaction product obtained in Example 50 and 50 parts by weight each of two ethylene/vinyl acetate copolymers (Evaflex 220 and 250, products of Mitsui Polychemical Co., Ltd.) were mixed under heat in the molten state to prepare a hot-melt adhesive. The hot-melt adhesive (melt viscosity 4500 centipoises, 180° C.) was melted and coated on aluminum substrates each having a thickness of 50 microns to a thickness of 15 microns. The coated surfaces were heat-sealed at 170° C. 1 kg/cm$^2$ for 2 seconds. The peel strength of the bonded product was measured by the T-peel method at various temperatures. The results are shown in Table 13.

TABLE 13

| Hot-melt adhesive | Peel strength (g/25 mm width) | | |
| --- | --- | --- | --- |
|  | 0° C. | 25° C. | 45° C. |
| Example 58 | 1300 | 1950 | 1150 |

EXAMPLE 59

Figure 11:
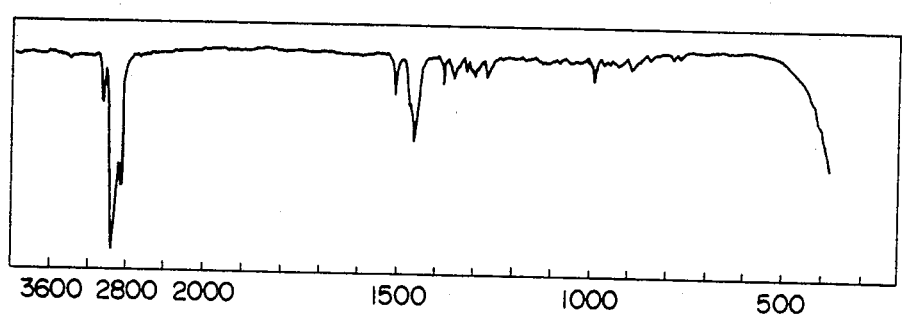

A 200 ml steel autoclave was charged with 10 g of 9-methyltetracyclo[5.2.1.1$^{3,6}$,0$^{2,7}$]dodec-3 (or 4-)ylbenzene obtained in Example 33, 20 g of Mitsui Hexane and 1 g of a sulfur-resistant nickel catalyst ("N-113B", a product of NIkki Chemical Co., Ltd.) as a hydrogenation catalyst, and hydrogenation was carried out at a reaction temperature of 200° C. and a pressure of 40 kg/cm$^2$-G for a period of 4 hours. After cooling, deashing and nitrogen purging, the catalyst was separated by filtration. The filtrate was distilled and 9 g of a colorless distillate was obtained at a column temperature of 170° C. and a pressure of 4 mmHg. From its molecular weight of 224 (theory 224) and its infrared spectrum (shown in FIG. 11), the distillate was determined to be 9-methyl-tetracyclo[6.2.1.1$^{3,6}$,0$^{2,7}$]dodec-3 (or 4-)ylcyclohexane.

EXAMPLE 60

A 200 ml steel autocalve was charged with 20 g of the mixture of toluenes substituted by 9-ethyl-tetracyclo[6.2.1$^{3,6}$,0$^{2,7}$]dodec-3 (or 4-)ylbenzene obtained in Example 36, 20 g of Mitsui Hexane and 2 g of a sulfurresistant nickel catalyst ("N112B", a product of Nikki Chemical Co., Ltd.) as a hydrogenation catalyst, and hydrogenation was arried out at a reaction temperature of 200° C. and a pressure of 40 kg/cm$^2$-G for a period of 4 hours. After cooling, deashing and nitrogen purging, the catalyst was separated by filtration. The filtrate was distilled to remove hexane and give 19.5 g of a colorless liquid resin ($n_D^{25}=1.5148$). Analysis of the resin by gel permeation chromatography showed that it consisted of 92.5% of methylcyclohexane monosubstituted by 9-ethyltetracyclo[6.2.1$^{3,6}$.0$^{2,7}$]dodec-3 (or 4)-yl, 6.0% of methylcyclohexane disubstituted by 9-ethyltetracyclo[6.2.1$^{3,6}$.0$^{2,7}$]dodec-3 (or 4)-yl, and 1.5% of other components.

Figure 12:
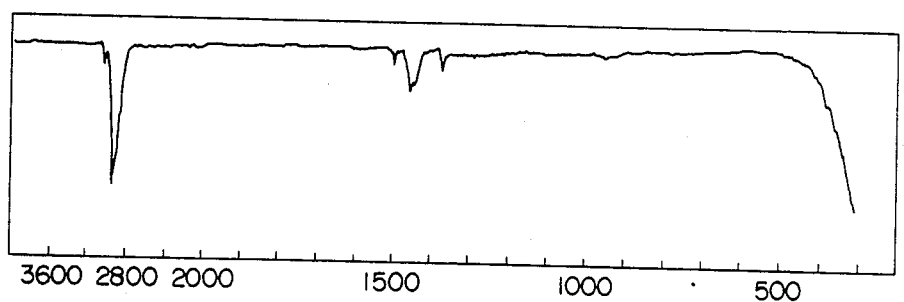

The infrared spectrum of the resulting resin is shown in FIG. 12.

EXAMPLES 61-62

One hundred parts by weight of SEBS block copolymer ("G-1657", a product of Shell Chemical Co.), 57 parts by weight of a commercial hydrogenated petroleum resin ("Arkon P-70", a product of Arakawa Chemical Co., Ltd.), 1 part by weight of a stabilizer ("Irganox 1010", a product of Ciba-Geigy) and 129 parts by weight of each of the novel hydrogenated substituted aromatic hydrocarbons obtained in Examples 59 and 60 were kneaded at 150° C. for 30 minutes by a kneader to prepare an adhesive.

The adhesive was heat-melted (for 20 minutes) on a polyester film (25 microns in thickness) on a hot plate kept at 195° C., and coated to a thickness of 30±5 microns by means of an applicator.

The properties of the adhesive were evaluated by the testing methods shown in Examples 9 and 26. The results are shown in Table 14.

TABLE 14

| Hydrogenated substituted aromatic hydrocarbon | Example 61 Example 59 | Example 62 Example 60 |
| --- | --- | --- |
| Compatibility | | |
| Tack (ball No. at 20° C.) | 9 | 8 |
| Adhesion strength (g/25 mm width at 20° C.) | 1,050 | 1,100 |
| Cohesive force (mm/2HR at 20° C.) | 0.1 | 0.1 |

What is claimed is:

1. An aromatic hydrocarbon in which at least one hydrogen atom on the ring is substituted by a group selected from the class consisting of unsubstituted or lower alkyl-substituted tricyclo[5.2.1.0$^{2,6}$]dec-3-yl, tricyclo[5.2.1.0$^{2,6}$]dec-4-yl, tetracyclo[6.2.1.1$^{3,6}$.0$^{2,7}$]dodec-4-yl and tetracyclo[6.2.1.1$^{3,6}$.0$^{2,7}$]dodec-5-yl groups, or its hydrogenation product.

2. The compound of claim 1 wherein the unsubstituted or lower alkyl-substituted tricyclo[5,2,1,0$^{2,6}$]dec-3-yl group is represented by the following formula (1)

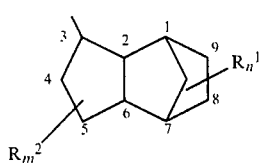

(1)

wherein $R^1$ is a lower alkyl group substituted at at least one of 1- and 7- to 10-positions, $R^2$ is a lower alkyl group substituted at at least one of 2- to 6-positions, n is 0 or an integer of 1 to 5 and m is 0 or an integer of 1 to 5, provided that when n is an integer of 2 to 5, the $R^1$ groups may be identical or different and when m is an integer of 2 to 5, the $R^2$ groups may be identical or different.

3. The compound of claim 1 wherein the unsubstituted or lower alkyl-substituted tricyclo[5.2.1.0$^{2,6}$]dec-4-yl group is represented by the following formula (2)

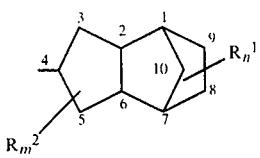

(2)

wherein $R^1$ is a lower alkyl group substituted at at least one of 1- and 7- to 10-positions, $R^2$ is a lower alkyl group substituted at at least one of 2- to 6-positions, n is 0 or an integer of 1 to 5 and m is 0 or an integer of 1 to 5, provided that when n is an integer of 2 to 5, the $R^1$ groups may be identical or different and when m is an integer of 2 to 5, the $R^2$ groups may be identical or different.

4. The compound of claim 1 wherein the unsubstituted or lower alkyl-substituted tetracyclo[6.2.1.1$^{3,6}$.0$^{2,7}$]dodec-4-yl group is represented by the following formula (3)

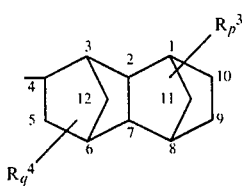

(3)

wherein $R^3$ is a lower alkyl group substituted at at least one of 1-, 2- and 7- to 11-positions, $R^4$ is a lower alkyl group substituted at at least one of 3- to 6- and 12-positions, p is 0 or an integer of 1 to 7 and q is 0 or an integer of 1 to 5, provided that when p is an integer of 2 to 7, the $R^3$ groups may be identical or different and when q is an integer of 2 to 5, the $R^4$ groups may be identical or different.

5. The compound of claim 1 wherein the unsubstituted or lower alkyl-substituted tetracyclo[6.2.1.1$^{3,6}$.0$^{2,7}$]dodec-5-yl group is represented by the following formula (4)

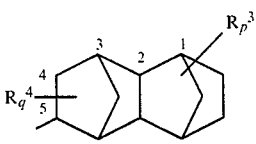

(4)

wherein $R^3$ is a lower alkyl group substituted at at least one of 1-, 2- and 7- to 11-positions, $R^4$ is a lower alkyl group substituted at at least one of 3- to 6- and 12-positions, p is 0 or an integer of 1 to 7 and q is 0 or an integer of 1 to 5, provided that when p is an integer of 2 to 7, the $R^3$ groups may be identical or different and when q is an integer of 2 to 5, the $R^4$ groups may be identical or different.

6. The compound of claim 1 wherein the lower alkyl group has 1 to 6 carbon atoms.

7. The compound of claim 1 wherein the aromatic hydrocarbon skeletal portion of the aromatic hydrocarbon is benzene, naphthalene, anthracene, biphenyl, terphenyl or indane.

8. The aromatic hydrocarbon of claim 1 which is represented by the following formula

(A)

herein Ar represents an aromatic hydrocarbon ring, R is a lower alkyl group having 1 to 6 carbon atoms or a hydroxyl group, X is a group selected from the class consisting of unsubstituted or $C_1$-$C_6$ alkyl-substituted tricyclo[5.2.1.0$^{2,6}$]dec-3-yl, tricyclo[5.2.1.0$^{2,6}$]dec-4-yl, tetracyclo[6.2.1.1$^{3,6}$.0$^{2,7}$]dodec-4-yl and tetracyclo[6.2.1.1$^{3,6}$.0$^{2,7}$]dodec-5-yl groups, r is 0, 1, 2 or 3, and l is 1, 2 or 3; or a hydrogenation product thereof.

9. The compound of claim 8 wherein Ar is a benzene ring.

10. The compound of claim 9 wherein R is a methyl group.

11. An additive for adhesives, said additive being composed of an aromatic hydrocarbon in which at least one hydrogen atom on the ring is substituted by a group selected from the class consisting of unsubstituted or lower alkyl-substituted tricyclo[5.2.1.0$^{2,6}$]dec-3-yl, tricyclo[5.2.1.0$^{2,6}$]dec-4-yl, tetracyclo 6.2.1.1$^{3,6}$.0$^{2,7}$]dodec-4-yl and tetracyclo[6.2.1.1$^{3,6}$.0$^{2,7}$]dodec-5-yl groups, or its hydrogenation product.

* * * * *